United States Patent
Adler et al.

(10) Patent No.: US 9,864,140 B2
(45) Date of Patent: *Jan. 9, 2018

(54) MINIATURE OPTICAL ELEMENTS FOR FIBER-OPTIC BEAM SHAPING

(71) Applicant: LightLab Imaging, Inc., Westford, MA (US)

(72) Inventors: Desmond Adler, Melrose, MA (US); Stephen McCartin, Chelmsford, MA (US); Christopher Petersen, Carlisle, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/198,581

(22) Filed: Jun. 30, 2016

(65) Prior Publication Data

US 2016/0313507 A1 Oct. 27, 2016

Related U.S. Application Data

(63) Continuation of application No. 14/744,861, filed on Jun. 19, 2015, now Pat. No. 9,404,731, and a (Continued)

(51) Int. Cl.
G02B 6/26 (2006.01)
G02B 6/32 (2006.01)
(Continued)

(52) U.S. Cl.
CPC .............. *G02B 6/262* (2013.01); *A61B 1/005* (2013.01); *A61B 1/00137* (2013.01); *A61B 1/07* (2013.01);
(Continued)

(58) Field of Classification Search
CPC .............. G02B 27/005; G02B 27/0911; G02B 27/0955; G02B 27/0977; G02B 27/0994;
(Continued)

(56) References Cited

U.S. PATENT DOCUMENTS 4,548,473 A 10/1985 Lo et al.
4,878,893 A 11/1989 Chin
(Continued)

FOREIGN PATENT DOCUMENTS

EP 0689797 1/1996
JP 63-127201 5/1988
(Continued)

OTHER PUBLICATIONS

Lieb et al., "A high numerical aperture parbolic mirror as imaging device for confocal microscopy", Optics Express, 8:7, pp. 458-474 (2001).
(Continued)

*Primary Examiner* — Akm Enayet Ullah
*Assistant Examiner* — Michael Mooney
(74) *Attorney, Agent, or Firm* — K&L Gates LLP

(57) ABSTRACT

In part, the invention relates to optical caps having at least one lensed surface configured to redirect and focus light outside of the cap. The cap is placed over an optical fiber. Optical radiation travels through the fiber and interacts with the optical surface or optical surfaces of the cap, resulting in a beam that is either focused at a distance outside of the cap or substantially collimated. The optical elements such as the elongate caps described herein can be used with various data collection modalities such optical coherence tomography. In part, the invention relates to a lens assembly that includes a micro-lens; a beam director in optical communication with the micro-lens; and a substantially transparent film or cover. The substantially transparent film is capable of bi-direction-
(Continued)

ally transmitting light, and generating a controlled amount of backscatter. The film can surround a portion of the beam director.

20 Claims, 20 Drawing Sheets

Related U.S. Application Data continuation of application No. 14/052,411, filed on Oct. 11, 2013, now Pat. No. 9,091,524, and a continuation of application No. 12/765,501, filed on Apr. 22, 2010, now Pat. No. 8,582,934, and a continuation-in-part of application No. 11/983,526, filed on Nov. 12, 2007, now Pat. No. 7,813,609, and a continuation-in-part of application No. PCT/US2008/012701, filed on Nov. 12, 2008.

(51) Int. Cl.
*G02B 6/36* (2006.01)
*G01B 9/02* (2006.01)
*G02B 6/42* (2006.01)
*A61B 5/00* (2006.01)
*G02B 23/24* (2006.01)
*G02B 27/09* (2006.01)
*A61B 1/00* (2006.01)
*A61B 1/005* (2006.01)
*A61B 1/07* (2006.01)
*A61B 5/02* (2006.01)
*G02B 27/00* (2006.01)
*G02B 23/26* (2006.01)
*A61B 6/00* (2006.01)
*G02B 5/08* (2006.01)

(52) U.S. Cl.
CPC .......... *A61B 5/0066* (2013.01); *A61B 5/0068* (2013.01); *A61B 5/0071* (2013.01); *A61B 5/0084* (2013.01); *A61B 5/02007* (2013.01); *A61B 5/6852* (2013.01); *A61B 5/6876* (2013.01); *G01B 9/02091* (2013.01); *G02B 6/32* (2013.01); *G02B 6/4204* (2013.01); *G02B 6/4206* (2013.01); *G02B 6/4214* (2013.01); *G02B 23/2423* (2013.01); *G02B 23/26* (2013.01); *G02B 27/005* (2013.01); *G02B 27/095* (2013.01); *G02B 27/0911* (2013.01); *G02B 27/0955* (2013.01); *G02B 27/0977* (2013.01); *G02B 27/0994* (2013.01); *A61B 6/504* (2013.01); *G02B 5/08* (2013.01)

(58) Field of Classification Search
CPC .. G02B 27/095; G02B 23/2423; G02B 23/26; G02B 5/08; A61B 5/0066; A61B 5/0068; A61B 5/0071; A61B 5/0084; A61B 5/02007; A61B 5/6852; A61B 5/6876
USPC ............ 385/27, 31, 33, 39, 53, 78, 79, 902; 356/477, 479, 614; 600/170, 407, 425
See application file for complete search history.

(56) References Cited

U.S. PATENT DOCUMENTS

| | | |
|---|---|---|
| 5,037,174 A | 8/1991 | Thompson |
| 5,228,441 A | 7/1993 | Lundquist |
| 5,321,501 A | 6/1994 | Swanson et al. |
| 5,342,355 A | 8/1994 | Long |
| 5,368,480 A | 11/1994 | Balfour et al. |
| 5,425,723 A | 6/1995 | Wang |
| 5,459,570 A | 10/1995 | Swanson et al. |
| 5,464,404 A | 11/1995 | Abela et al. |
| 5,465,147 A | 11/1995 | Swanson |
| 5,509,093 A | 4/1996 | Miller et al. |
| 5,509,917 A | 4/1996 | Cecchetti et al. |
| 5,518,810 A | 5/1996 | Nishihara et al. |
| 5,632,767 A | 5/1997 | Sinofsky |
| 5,643,253 A | 7/1997 | Baxter et al. |
| 5,683,290 A | 11/1997 | Kanda et al. |
| 5,727,989 A | 3/1998 | Ohno et al. |
| 5,746,737 A | 5/1998 | Saadat |
| 5,748,598 A | 5/1998 | Swanson et al. |
| 5,772,657 A | 6/1998 | Hmelar et al. |
| 5,784,352 A | 7/1998 | Swanson et al. |
| 5,822,072 A | 10/1998 | Dai et al. |
| 5,833,520 A | 11/1998 | Kanda et al. |
| 5,833,683 A | 11/1998 | Fuller et al. |
| 5,908,415 A | 6/1999 | Sinofsky |
| 5,947,959 A | 9/1999 | Sinofsky |
| 5,956,355 A | 9/1999 | Swanson et al. |
| 5,964,747 A | 10/1999 | Eaton et al. |
| 6,111,645 A | 8/2000 | Tearney et al. |
| 6,134,003 A | 10/2000 | Tearney et al. |
| 6,152,951 A | 11/2000 | Hashimoto |
| 6,160,826 A | 12/2000 | Swanson et al. |
| 6,184,923 B1 | 2/2001 | Miyazaki |
| 6,191,862 B1 | 2/2001 | Swanson et al. |
| 6,282,011 B1 | 8/2001 | Tearney et al. |
| 6,283,957 B1 | 9/2001 | Hashimoto |
| 6,287,300 B1 | 9/2001 | Kondo et al. |
| 6,301,406 B1 | 10/2001 | Irie et al. |
| 6,317,550 B2 | 11/2001 | Irie et al. |
| 6,348,960 B1 | 2/2002 | Etori et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,600,856 B1 | 7/2003 | Lewis et al. |
| 6,692,824 B2 | 2/2004 | Benz et al. |
| 6,724,959 B1 | 4/2004 | Takahashi et al. |
| 6,763,261 B2 | 7/2004 | Casscells, III et al. |
| 6,783,522 B2 | 8/2004 | Fischell |
| 6,797,931 B2 | 9/2004 | Iizuka et al. |
| 6,856,728 B2 | 2/2005 | Zhang |
| 6,879,851 B2 | 4/2005 | McNamara et al. |
| 6,888,119 B2 | 5/2005 | Iizuka et al. |
| 6,891,984 B2 | 5/2005 | Petersen et al. |
| 6,904,197 B2 | 6/2005 | Bhagavatula et al. |
| 6,932,809 B2 | 8/2005 | Sinofsky |
| 6,942,657 B2 | 9/2005 | Sinofsky et al. |
| 6,974,557 B1 | 12/2005 | Webler et al. |
| 7,062,135 B2 | 6/2006 | Caracci et al. |
| 7,066,819 B2 | 6/2006 | Ueda et al. |
| 7,108,677 B2 | 9/2006 | Courtney et al. |
| 7,121,947 B2 | 10/2006 | Ueda et al. |
| 7,208,333 B2 | 4/2007 | Flanders et al. |
| 7,218,822 B2 | 5/2007 | Treado |
| 7,221,839 B2 | 5/2007 | Ohta et al. |
| 7,235,067 B2 | 6/2007 | Morris et al. |
| 7,241,286 B2 | 7/2007 | Atlas |
| 7,254,296 B2 | 8/2007 | Lam et al. |
| 7,298,478 B2 | 11/2007 | Gilbert et al. |
| 7,311,625 B2 | 12/2007 | Nosaka et al. |
| 7,355,699 B2 | 4/2008 | Gilbert et al. |
| 7,362,516 B2 | 4/2008 | Gal et al. |
| 7,407,440 B2 | 8/2008 | White |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,421,186 B2 | 9/2008 | Boutoussov et al. |
| 7,460,748 B2 | 12/2008 | Tang |
| 7,463,801 B2 | 12/2008 | Brekke et al. |
| 7,492,522 B2 | 2/2009 | Gilbert et al. |
| 7,507,038 B2 | 3/2009 | Nakamura et al. |
| 7,532,920 B1 | 5/2009 | Ainsworth et al. |

(56) References Cited

U.S. PATENT DOCUMENTS

| | | |
|---|---|---|
| 7,576,861 B2 | 8/2009 | Gilbert et al. |
| 7,625,366 B2 | 12/2009 | Atlas |
| 7,627,208 B2 | 12/2009 | Kuroiwa |
| 7,715,896 B2 | 5/2010 | Ramzipoor et al. |
| 7,733,497 B2 | 6/2010 | Yun et al. |
| 7,746,914 B2 | 6/2010 | Muendel |
| 7,813,609 B2 | 10/2010 | Petersen et al. |
| 7,848,791 B2 | 12/2010 | Schmitt et al. |
| 7,916,387 B2 | 3/2011 | Schmitt et al. |
| 7,935,060 B2 | 5/2011 | Schmitt et al. |
| 7,967,743 B2 | 6/2011 | Ishihara |
| 8,021,366 B2 | 9/2011 | Phan |
| 8,358,461 B2 | 1/2013 | Huber et al. |
| 8,582,934 B2 * | 11/2013 | Adler .................. A61B 5/0066 356/614 |
| 9,091,524 B2 * | 7/2015 | Adler .................. A61B 5/0066 |
| 2002/0161351 A1 | 10/2002 | Samson et al. |
| 2003/0074924 A1 | 4/2003 | Melville et al. |
| 2005/0201662 A1 | 9/2005 | Petersen et al. |
| 2005/0251116 A1 | 11/2005 | Steinke et al. |
| 2006/0095065 A1 | 5/2006 | Tanimura et al. |
| 2006/0203859 A1 | 9/2006 | Cable et al. |
| 2007/0232893 A1 | 10/2007 | Tanioka |
| 2008/0154249 A1 | 6/2008 | Cao |
| 2008/0267562 A1 | 10/2008 | Wang et al. |
| 2009/0135429 A1 | 5/2009 | Masuda |
| 2009/0262361 A1 | 10/2009 | Tanioka et al. |
| 2011/0206321 A1 | 8/2011 | Reever |

FOREIGN PATENT DOCUMENTS

| | | |
|---|---|---|
| JP | 2001-264246 | 9/2001 |
| JP | 2001-513659 | 9/2001 |
| JP | 2009-74886 | 4/2009 |
| WO | 98/12968 | 4/1998 |
| WO | 2008/081653 | 7/2008 |
| WO | 2008114725 | 9/2008 |

OTHER PUBLICATIONS

Tumlinson et al., "Endoscope-tip interferometer for ultrahigh resolution frequency domain optical coherence tomography in mouse colon", Optics Express, 14:4, pp. 1878-1887 (2006).

English translation of Office Action of Japanese Patent Office for Application No. 2013-506128, dated Feb. 12, 2014 (17 pages).

Japanese Office Action and English translation dated Dec. 16, 2014 for Japanese Patent Application No. 2013-506128 (12 pgs.).

English translation of Office Action of Japanese patent Office for Patent Application No. 2015-242284, dated Dec. 20, 2016 (5 pages).

* cited by examiner

MINIATURE OPTICAL ELEMENTS FOR FIBER-OPTIC BEAM SHAPING

CROSS-REFERENCE TO RELATED APPLICATIONS

This application is a continuation of U.S. patent application Ser. No. 14/744,861 filed Jun. 19, 2015, which is a continuation of U.S. patent application Ser. No. 14/052,411, filed Oct. 11, 2013, now U.S. Pat. No. 9,091,524, which is a continuation of U.S. patent application Ser. No. 12/765,501 filed Apr. 22, 2010, now U.S. Pat. No. 8,582,934, which is a continuation-in-part of U.S. patent application Ser. No. 11/983,526, filed Nov. 12, 2007, now U.S. Pat. No. 7,813,609. This application is also a continuation-in-part of International Application No. PCT/US2008/012701 filed on Nov. 12, 2008. The entire contents of the above-identified applications are incorporated by reference herein.

FIELD OF THE INVENTION

This invention relates generally to optical elements, the design and manufacture of optical elements, and methods of using the same. In addition, the invention also relates to using optical elements to collect data with respect to a sample of interest.

BACKGROUND OF THE INVENTION

Optical analysis methods such as interferometric methods deliver light onto a sample of interest, and further require collection of a portion of the light returned from the sample. Due to the size and complexity of many light sources and light analysis devices, they are typically located remotely from the sample of interest. This is especially apparent when the sample of interest is an internal part of a larger object, such as biological tissue inside of a living organism. One method of optically analyzing internal parts is to guide light from a remote light source onto the sample using a thin optical fiber that is minimally disruptive to the normal function of the sample due to the diminutive cross-section of the optical fiber. An example of such a method is the optical analysis of a luminal organ, such as a blood vessel, using a fiber-optic catheter that is connected on one end to a light source outside of the body while the other end is inserted into the vessel.

A significant barrier to conducting optical analysis of internal regions, such as lumens, is the design and low-cost manufacture of miniature optical devices for focusing or collimating light. Many types of optical analysis, such as imaging and spectroscopy, require that the light incident on the sample be focused at a particular distance or substantially collimated. Since light radiating from the tip of a standard optical fiber will diverge rapidly, a miniature optical system can be coupled to the fiber to provide a focusing or collimating function. Additionally, it is often desirable to analyze a sample location that is not directly in line with the optical axis of the fiber, such as the analysis of the luminal wall of a thin blood vessel. In these situations, a means for substantially altering the direction of the light is used in addition to a means for focusing or collimating the light radiating from the tip of an optical fiber.

Many methods have been previously described for manufacturing miniature optical systems suitable for attachment to an optical fiber that provide some of the functionality described above. These methods generally provide a beam focusing means using one of three methods: 1) using a graded-index (GRIN) fiber segment; 2) directly shaping the fiber tip into a lens; or 3) using a miniature bulk lens. A beam directing means is generally provided using one of four methods: 1) using total internal reflection (TIR) of light from the angled end face of the fiber using an angled, reflective surface; 3) using a miniature bulk mirror; or 4) using a reflective coating on the fiber tip. These methods, however, have numerous inherent limitations, including excessive manufacturing cost, excessive size, or insufficient freedom to select the focal spot size and focal distance.

There are many miniature optical systems known in the art that can be used for analysis of internal luminal structures. Each optical system can be conceptually divided into a beam focusing means and a beam directing means. Light is passed from an external light source to the internal lumen through one or more optical illumination fibers, which may be single mode or multimode in nature. The illumination fiber is in communication with the miniature optical system, which focuses and directs the beam into the luminal wall. Light is returned from the lumen to an analysis apparatus outside the body using the same fiber, or using other fibers co-located with the illumination fiber. In one type of miniature optical system design, the focusing means and directing means are performed by separate optical elements. In another type of design, the focusing means and directing means are performed by the same element.

Several features of existing optical systems are undesirable. For example, in some devices all of the optical elements must be of a diameter similar to the optical fiber (the diameter often being similar to 125 μm) in order to minimize the overall system size. This greatly reduces the options available for selecting the focusing element, beam expander, and beam director and therefore limits the range of focal spot sizes and working distances achievable by the design. Additionally, these extremely small elements are fragile, difficult to handle, and prone to break during manufacturing and operation. Third, in many embodiments an air gap must be provided in order to use TIR for beam redirection. This requires a tight seal to be maintained between the fiber and the other element to maintain the air gap. This can be problematic when the device is immersed in water, blood, or stomach acid, or when the device is rotated or translated at high speed in order to form an image. Fourth, GRIN focusing elements have refractive index profiles that are rotationally symmetric, making it impossible to correct for cylindrical aberrations induced on the beam. The overall effect of these drawbacks is that certain miniature optical systems are expensive, difficult to manufacture, prone to damage, and do not produce a circular output at the focal plane.

In addition to the drawbacks listed above, conventional lensed surfaces can only provide small radii of curvature and are largely limited to spherical geometries. Additionally, the beam cannot expand to a size significantly larger than the single mode fiber diameter (often 125 μm) at any point in the optical system. These limitations result in a lens system with a limited working distance and significant spherical aberrations.

As described above, there are significant limitations to currently known miniature optical systems used for conducting optical analysis or imaging. Accordingly, a need exists for optical elements that overcome the limitation of existing optical devices.

SUMMARY OF THE INVENTION

In part, the present invention provides a unitary optical element (or cap) having an internal cavity that slides over the end of an optical fiber for internal or external analysis of a sample. The cap includes integrated surface features for altering the beam direction as well as focusing or collimating the light at a prescribed width at a prescribed distance away from the cap. The cap is sufficiently small to prevent disruption or damage to sensitive samples, such as internal body tissue or luminal organs. Since the cap is a single monolithic element in an embodiment, it can be fabricated using low-cost methods such as injection molding. A significant cost advantage and improvement in manufacturing repeatability compared to previously-described methods is achieved.

One embodiment of the invention provides an optical element such as a cap, a cover, or an elongated member with a distal curved end face or surface. The optical element can be manufactured from a single piece of material that can be fixed to and receive a section of optical fiber. Specifically, the cap has an open end that receives the fiber, a length of solid material that is selected to be substantially optically transparent, and a closed end with a curved reflective end surface that acts both as a lens and a mirror. In one embodiment, the curved reflective surface is shaped to have the focusing properties of a lens and coated to reflect (or partially reflect) incident light.

Light radiates from the optical fiber, travels through the solid material, and impinges on the curved reflective end surface. The curvature of the lensed surface can be designed to focus or substantially collimate the incident light. The lensed surface can also be tilted relative to the propagation direction of the light radiating from the fiber tip. The tilt angle is selected to reflect the light such that it exits the cap through a side face and reaches a focus at a desired distance away from the side face.

The reflective property of the distal surface is obtained by coating the exterior of the curved end surface with a reflective material such as metal or a dielectric material. Additionally, the curvature of the lensed surface can be different along each of two orthogonal axes. Further, the curvature of one axis can be independently adjusted to compensate for optical distortions imparted on the light as it exits through the substantially cylindrical side face of the cap. The single-piece construction of the cap makes it amenable to manufacturing by low-cost methods such as injection molding.

In one embodiment, the invention relates to an optical beam directing element. The optical beam directing element includes an elongate unitary cap comprising a cylindrical outer surface having a longitudinal axis comprising, a proximal endface defining an annular opening and a distal endface comprising a beam directing surface, the elongate unitary cap defining a solid section and a first cavity section defining a volume extending to a boundary of the solid section, the volume sized to surround an optical fiber having a fiber endface and receive the optical fiber, wherein the beam directing surface is angled and positioned relative to the fiber endface such that light received from the fiber endface is directed a working distance D from the cylindrical outer surface to form a focal spot having diameter w.

In one embodiment, the elongate unitary cap is formed from a material selected from the group consisting of acrylic, polycarbonate, polystyrene, polyetherimide, polymethylpentene, and glass. D can range from about 0 μm to about 30 mm. In one embodiment, w ranges from about 3 μm to about 100 μm. The beam directing element can further include a stationary sheath and an optical fiber fixedly disposed within the volume, the optical fiber and elongate unitary cap arranged to rotate within the stationary sheath. In one embodiment, at least a portion of the beam directing surface is coated with a reflecting coating. The beam directing element can further include a lensed surface disposed within the cylindrical outer surface and formed from the boundary. In one embodiment, the beam directing surface is substantially flat. The reflecting coating can include a partially transmissive coating.

In one embodiment, the partially transmissive coating splits the light from the fiber endface into a first beam directed to the working distance D from the cylindrical outer surface to form the focal spot having diameter w and a second beam directed to a working distance D' from the cylindrical outer surface to form a focal spot having diameter w'. Further, a beam incident from the fiber endface can be split based upon the intensity of the incident beam or the wavelength of the incident beam. In one embodiment, a partially reflective coating is disposed on a distal section of the cylindrical outer surface at a position such that a beam directed from the beam forming surface passes through and reflects back from the partially reflective coating. A partially reflective coating can disposed within the volume along a portion of the boundary. In one embodiment, the beam directing surface is positioned within the volume or the solid section. A second cavity section can be defined within the solid section such that the beam directing surface is partially shielded by a portion of the cylindrical outer surface that surrounds the second cavity section. Further, the beam directing surface is shaped to substantially remove cylindrical optical distortion induced by light propagating from the beam directing surface through the cylindrical outer surface and the stationary sheath. In one embodiment, the beam directing surface is selected from the group consisting of biconic asphere, asphere, biconic Zernike, Fresnel, and non-uniform rational B-spline.

In one aspect, the invention relates to a method of collecting optical data from a test sample in situ. The method includes the steps of providing an optical fiber including a core, the optical fiber being adapted to convey an optical beam at a first diameter; providing an elongate unitary cap comprising a cylindrical outer surface and an annular opening that is fixedly and optically coupled to the optical fiber by receiving and encircling a length of the optical fiber within a cavity defined within the cap; and transmitting the optical beam to a beam directing surface such that a first optical beam is directed a working distance D from the cylindrical outer surface to form a focal spot having diameter w. In one embodiment, the method further includes the step of splitting the optical beam such that a second optical beam is directed a working distance D' from the cylindrical outer surface to form a focal spot having diameter w'. In one embodiment, method further includes the step of collecting optical coherence tomography data using the first optical beam. In one embodiment, the method further includes the step of generating one of a reference signal in response to a reflecting element disposed within the unitary cap, the reflecting element acting as an interferometer arm in an optical coherence tomography imaging system. In one embodiment, the method further includes the step of generating one of a calibration signal in response to a reflecting element disposed within the unitary cap, the calibration signal being used to adjust the reference arm path length to match the sample arm path length in an optical coherence tomography imaging system.

Summary of Reference Reflector/Scattering Element Embodiments

In one aspect, the invention relates to fiber optic imaging probe having an elongated section and a proximal and a distal end, the probe comprising a thin controlled optical scattering material applied to the distal end.

In another aspect, the invention relates to an optical element. The optical element includes a membrane or cover having a first surface and a second surface. The membrane includes a polymer and at least one back-scattering element for controlled optical back-scattering disposed therein. Further, the membrane allows transmission of substantially undistorted imaging light.

The aspects of the invention described herein can include further embodiments. For example, the optical element can further include a plurality of back-scattering elements wherein the at least one back-scattering element and each of the plurality of back-scattering elements is a particle having a particle dimension, the plurality of back-scattering elements disposed within the polymer. In one embodiment, the membrane is shaped to form a curved surface suitable for engulfing, surrounding, enveloping or otherwise covering an optical fiber endface or micro-lens.

The particle dimension, in some preferred embodiments, is less than about 1.5 µm. Further, the particles can include titanium, zinc, aluminum, and/or other materials suitable for scattering light. The plurality of scattering elements can have a concentration of about 0.1% doping concentration by volume. The optical element can further include an elongate member, wherein the membrane is shaped to form a sheath within which the elongate member is disposed to form a portion of a probe tip.

In one aspect, the invention relates to an optical element. The optical element includes a curved cover having a first surface and a second surface, the cover forming a portion of an imaging probe, the cover comprising a polymer and at least one back-scattering element for controlled optical back-scattering disposed therein such that a reference point is generated for an imaging system from the optical back-scattering, the cover allowing transmission of substantially undistorted imaging light.

In another aspect, the invention relates to an imaging probe. The probe includes an elongate section having a first end and a second end; the second end forming a probe tip capable of intra-lumen imaging, the probe tip comprising a scattering material, the elongate section adapted to transmit light reflected by the scattering material to the first end of the elongate section.

In one embodiment, the elongate section is an optical fiber. The elongate section can be a sheath. Also, the probe can further include an optical fiber disposed within the sheath. The scattering material can include a plurality of light scattering particles dispersed in a matrix. The scattering particles can include titanium and/or other materials known to scatter light. Also, the matrix can include polyethylene terepthalate and/or other polymers such as urethane derivatives.

In one embodiment of an aspect of the invention, the controlled amount of backscatter is in an amount of light at least sufficient to generate a reference point in an imaging system for calibration of at least one imaging system parameter. The substantially transparent film can also include a plurality of scattering particles.

In still another aspect, the invention relates to a method of calibrating an optical coherence tomography system. The method includes generating scan data in response to light reflected from a sample, the reflected light passing through a bi-directional substantially transparent optical element; generating reference data in response to scattered light reflected from a scattering element disposed within the bi-directional substantially transparent optical element; and calibrating the optical coherence tomography system to determine the relative longitudinal position of the scattering element.

In one aspect, the invention relates to a method of fabricating an optical element. The method includes the steps of selecting a material suitable for intra-lumen use in an animal; selecting a dopant suitable for dispersion in the material, the dopant adapted to scatter light in response to an optical source; determining a dopant volume concentration such that a radial scan of a doped material generates a defined backscatter.

One embodiment of the invention provides an optical cap that can be fixed to an end of a section of optical fiber, the cap having an open end that receives the fiber, an internal curved surface in line with the optical fiber that acts as a lens, a length of solid material, and a closed end with a flat reflective end surface that acts as a mirror. In some embodiments, the reflective end surface is coated and in other embodiments it is uncoated. The curvature of the internal lensed surface is chosen to focus or substantially collimate light radiating from the end of the optical fiber. The reflective end surface is made to be reflective by coating the exterior of the end face with metal or a dielectric material. In one embodiment, the tilt angle theta between the end face and the axis of the fiber will generally be about 45 degrees+/−about 20 degrees.

Another embodiment of the invention provides an optical cap that can be fixed to an end of a section of optical fiber, the cap having an open end that receives the fiber, an internal curved surface in line with the optical fiber that acts as a lens, a length of solid material, and a closed end with a curved reflective end surface that acts as a second lens and a mirror. The internal lensed surface is curved along one or two orthogonal axes to provide a first focusing means acting on light radiating from the tip of the fiber. The end surface is also curved along one or two orthogonal axes to provide a second focusing means acting on light transmitted from the first lensed surface and through the length of solid material. In one embodiment, the end surface is made reflective by coating with a reflective material. In one embodiment, the reflective material may be a metal or a dielectric material. In one embodiment, the optical cap is a unitary cap. Further, the optical cap can be made from one or more pieces of material in some embodiments.

Still another embodiment of the invention provides an optical cap that can be fixed to an end of a section of optical fiber, the cap having an open end that receives the fiber, a length of solid material, and a closed end with a curved partially-reflective surface. Light radiates from the tip of the fiber, travels through the solid material, and impinges on the partially-reflective surface. A portion of the light is focused by way of the curvature of the surface, is reflected, and exits through a side face of the cap. Another portion of the light is refracted and transmitted through the end face of the cap. In this way, optical measurements can simultaneously be made along two different axes. The end face is made partially reflective by coating the surface with a thin layer of metal, a patterned layer of metal, or by coating with a thin dielectric film that is designed to partially transmit light.

An additional embodiment of the invention provides an optical cap that can be fixed to an end of a section of optical fiber, the cap having an open end that receives the fiber, a length of solid material, a closed end with a curved reflective surface, and a side face with a partially-reflecting or back-scattering coating. Light radiates from the tip of the fiber, travels through the solid material, and impinges on the reflective surface. The light is focused by way of the curvature of the surface, is reflected, and impinges on the coated side face of the cap. A portion of this light is transmitted by the coating and reaches a focal spot at a desired distance away from the cap. Another portion of the light is directly back-reflected or backscattered by the coating and travels internally back towards the curved end face. The light reflects again off the end face, is re-focused, and is partially coupled back into the end tip of the optical fiber.

In this way, a controlled amount of reflected or backscattered light can be generated at a known distance from the focal spot, which is advantageous for use as a calibration signal or interferometric reference field in analysis techniques such as optical coherence tomography. The end face is made reflective by coating with metal or a dielectric material. The side face is made partially reflective by partially coating with a material such as gold, aluminum, or other metals, or by coating with a thin dielectric film that is designed to partially transmit light, or by coating with a layer of small backscattering particles. Alternatively, the partially reflective property may be provided by a thin polymer tube that is impregnated with backscattering particles, the thin polymer tube being fixed over the outside of the optical cap. The thin polymer tube may be polyethylene terephthalate (PET), and the backscattering particles may be titanium dioxide. The reflective coating can also be selected from suitable dielectric reflective coatings. These dielectric reflective coatings can include multiple layers of dielectric material. For example alternative layers of $TiO_2$ and $SiO_2$ can be used in some embodiments to form a reflective coating.

Yet another embodiment of the invention provides an optical cap that can be fixed to an end of a section of optical fiber, the cap having an open end that receives the fiber, an internal surface with a partially-reflecting coating in line with the optical fiber, a length of solid material, a closed end with a curved reflective surface, and a side face with a partially-reflecting coating. Light radiates from the tip of the fiber and impinges on the internal partially-reflecting surface. A portion of the light is reflected or backscattered back into the fiber while another portion of the light is transmitted and travels through the solid material. In this way, a first amount of reflected or backscattered light can be generated at a known distance from the focal spot. The transmitted portion of the light then impinges on the reflective surface. The light is focused by way of the curvature of the surface, is reflected, and impinges on the coated side face of the cap.

With respect to this embodiment, a portion of this light is transmitted by the coating and reaches a focal spot at a desired distance away from the cap. Another portion of the light is directly back-reflected or backscattered by the coating and travels internally back towards the curved end face. The light reflects again off the end face, is re-focused, and is partially coupled back into the end tip of the optical fiber. In this way, a second amount of reflected or backscattered light can be generated at a known distance from the focal spot and at a known distance from the internal partially-reflective surface, which is advantageous for use as a calibration signal or interferometric reference field in analysis techniques such as optical coherence tomography. The end face is made reflective by coating with metal or a dielectric material. The side face and internal face are made partially reflective or backscattering by partially coating with a metal material, or by coating with a thin dielectric film that is designed to partially transmit light, or by coating with a layer of small backscattering particles.

In another embodiment, the invention also provides a method for using the various embodiments of the optical cap as a component in a fiberoptic imaging catheter, the fiberoptic imaging catheter being inserted into a luminal structure of a living body and connected to an optical coherence tomography system in order to obtain high-resolution images of the luminal structure.

Still another embodiment provides a means for protecting the lensed surface of the optical cap by partially or completely locating it within the body of the cap. The cap may have any suitable geometry and is not limited to cylindrical shaped caps. Partial protection of the lensed surface can be obtained by including an extension of the cylindrical body slightly proximal of the lensed surface. In one embodiment, partial protection of the lensed surface can be obtained by locating the lensed surface entirely within the cavity that receives the optical fiber. It is understood that any of the embodiments described above can be modified to include partial or complete protection of the lensed surface. These embodiments of the invention are no limited to protection related features. For example, recessing the lensed surface can make it easier to guide the cap distally in some embodiments.

The various embodiments described herein relate to subsystems for transmitting and receiving various types of electromagnetic radiation that can be directed through an optical fiber or similar waveguide. Accordingly, although reference may be made to radiation, optical radiation, light, or other types of electromagnetic radiation, these terms are not intended to limit the scope of the invention and instead encompass any type of light or electromagnetic radiation that can be sent or received by a lens or optical fiber or similar waveguide.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. The drawings associated with the disclosure are addressed on an individual basis within the disclosure as they are introduced.

DETAILED DESCRIPTION OF THE INVENTION

Figure 1:
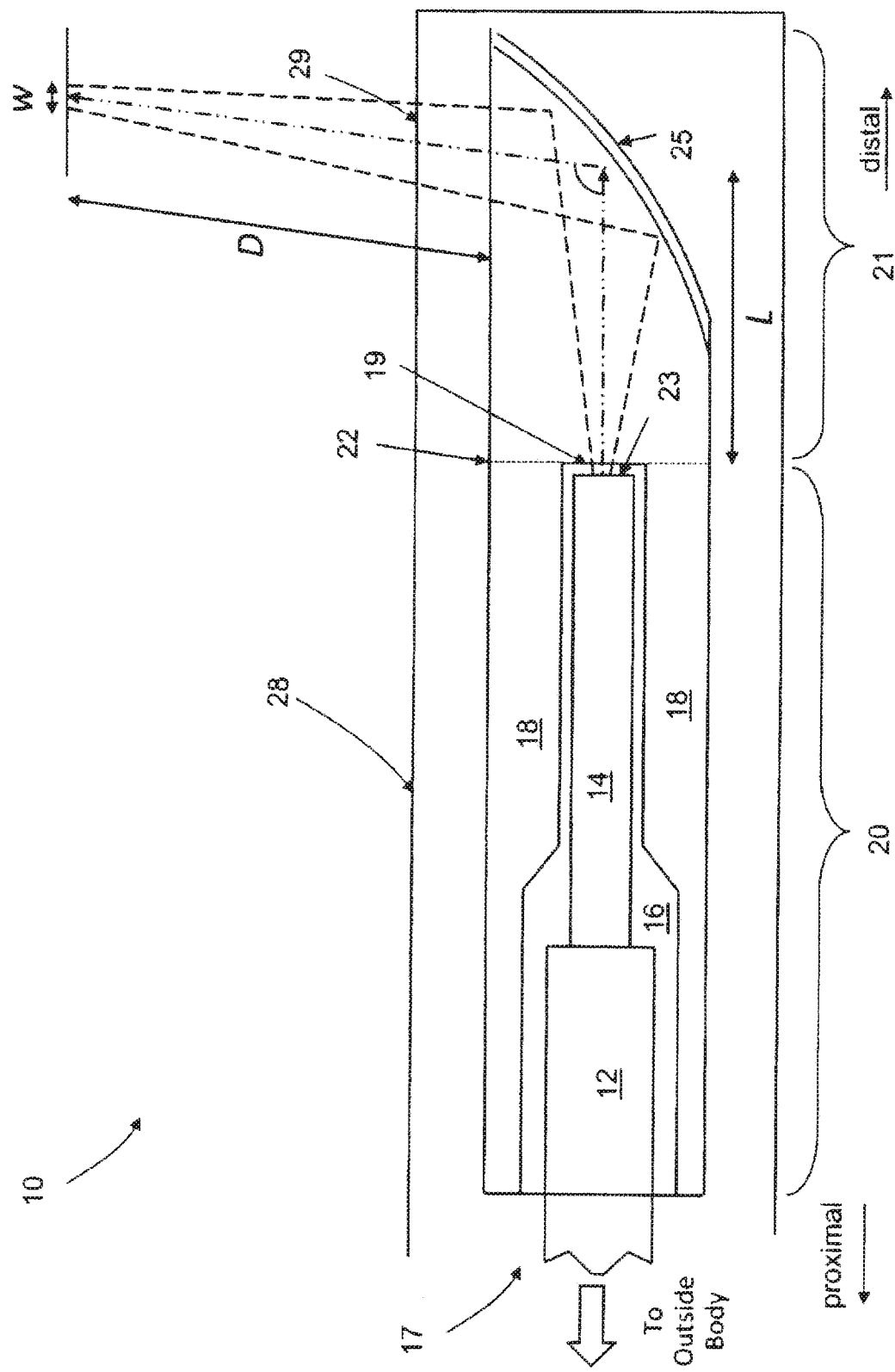
FIG. 1 is a two-dimensional cross-sectional schematic diagram depicting an optical subsystem for directing a beam of light along an optical fiber and through an elongate member defining a cavity according to an illustrative embodiment of the invention.

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention, rather the scope of the present invention is defined by the claims.

The use of sections or headings in the application is not meant to limit the invention; each section and heading can apply to any aspect, embodiment, or feature of the invention.

It should be understood that the order of the steps of the methods of the invention is immaterial so long as the invention remains operable. Moreover, two or more steps may be conducted simultaneously or in a different order than recited herein unless otherwise specified.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It should be understood that the terms "a," "an," and "the" mean "one or more," unless expressly specified otherwise.

The foregoing, and other features and advantages of the invention, as well as the invention itself, will be more fully understood from the description, drawings, and claims.

The development of advanced optical analysis or imaging methods such as confocal microscopy, single- and multi-photon fluorescence imaging, harmonic imaging, optical spectroscopy, and optical coherence tomography (OCT) have had a tremendous impact on industrial inspection, fundamental biology studies, and in vivo imaging of animals and humans. Although these methods are dissimilar in many ways, they share a common design feature that the incident light used to illuminate the sample of interest be focused or collimated. Focused light provides many advantages over unfocused light, including improved localization of incident light for obtaining better spatial resolution, and higher optical power density for generating increased signal levels.

A focused or collimated beam is generated by directing the output of a light source through a series of optical elements that together form an optical system. The elements of the optical system are selected to achieve a desired focal spot size, which occurs at a desired distance, referred to as the "working distance," away from the last element in the optical system. The working distance is shown at an angle in the figures. This is the preferred way to define working distance (parallel to the direction of beam propagation). One preferred embodiment will use a beam that exits the side of the cap at a forward angle of ~10 degrees. Each specific optical analysis application will have its own optimal spot size and working distance. Confocal microscopy, for example, requires small spot sizes close to 1 µm. OCT, on the other hand, requires moderate spot sizes of about 5-about 100 µm.

Although it is possible to obtain a wide range of spot sizes and working distances using optical systems comprised of conventional bulk lenses, many applications require flexible and miniaturized optical systems in order to analyze samples located inside of a larger object. Biomedicine is one example of a field where this requirement is often found. The optical analysis of luminal structures such as the esophagus, intestines, urinary tract, airway, lungs, and blood vessels can use light from an external light source that is transmitted via a flexible probe, focused with a miniature optical system, and returned through the flexible probe to a data analysis system outside the body.

Furthermore, it is often desirable to analyze the luminal wall instead of the contents of the lumen, for example imaging the intima and media of a blood vessel wall using OCT instead of imaging the blood contained in the vessel. This results in an additional design objective of directing the beam away from the longitudinal axis of the optical system or along another preferred direction (or range of directions). These types of optical probes are often referred to as "side-firing," "side-directed," "side-imaging," or "side-looking" The size of these lumens can be as small as several millimeters, such as in blood vessels, making the design of the miniature optical system quite challenging. In addition, the embodiments described herein are also suitable for use with various multi-fiber or fiber bundle embodiments. The various embodiments described below address these needs and others associated with probe components and beam formation.

Overview

In general, the invention relates to an optical element having an elongated three dimensional shape such as a cap. The optical element defines a cavity or channel. The optical element can be sized to receive an optical fiber portion and operatively direct and focus light. The optical element can be fixed to an optical fiber and used to both redirect and focus light outside of the cap and receive light from a sample of interest. The present invention provides methods for using the miniature optical cap and fiber as part of an insertable probe, which can in turn be used to conduct optical analysis of a luminal structure inside a living body. Other embodiments of the invention also relate to the design, manufacture, and use of such devices for delivering focused or substantially collimated light to a sample, and returning a portion of the light from the sample for processing with imaging or data collection systems. One exemplary non-limiting example of such a system is an optical coherence tomography (OCT) system.

Beam Forming Elements

FIG. 1 shows one embodiment of the invention suitable for forming a beam at a predetermined location. Specifically, an optical system 10 suitable for directing and collecting light or otherwise collecting data with respect to a sample of interest is shown. In the example shown, an optical fiber is connected on its proximal end to a light source (not shown). The optical fiber includes coated region 12, and a light-guiding core with cladding region 14. In one embodiment, the coated region 12 includes a polyimide material. As shown in FIG. 1, the coating has been partially removed to expose a portion of the core and cladding distal to the coated region 12. A protective material 16 such as an adhesive also surrounds the core and cladding 14 and/or the coated region 12 as shown in FIG. 1. The optical fiber guides optical radiation from a light source to the distal fiber segment, where a length of the coating has been removed by mechanical or chemical stripping. The fiber end face (alternatively, fiber tip) can be flat or, to prevent aberrations and unwanted backreflections, can be cleaved to a small angle, typically between about 8° and about 15°. This cleave operation can be performed with a fiber cleaver. In one embodiment, since such a cleave operation is quick and consistent it offers cost savings and manufacturing advantages.

In general, in part, the invention relates to a unitary optical element (alternatively, an optical probe element or cap) 18 formed from a transmissive material. In one embodiment, the unitary optical element or cap is elongate in shape. In other embodiments, the optical element or cap is spherical or semi-spherical. For example, in one embodiment, the cap is a sphere or a partially flattened sphere with a fiber-accepting hole formed in a non-diametrical direction, specifically a ½ radius down from the center of the sphere. However, any suitable cap geometry is possible. The optical element defines a bore or a channel that extends through a portion of optical element 18 before terminating at a wall or region 19 formed from the transmissive material. As shown, the fiber core and cladding 14 and coated region 12 are disposed within a volume defined in the cap 18 and enter the cap 18 through the annular opening 17 shown on the left side of the figure. Although the invention relates to various types and forms of such optical elements that define a channel, cavity or bore that partially encircles or surrounds an optical fiber, the terms "cap," "cover," "optical assembly," "beam former," "lens assembly," or other terminology may be used in a non-limiting manner herein.

Thus, in one embodiment the optical cap (alternatively, an optical element) 18 includes a fiber containing section 20 and a beam forming (or solid) section 21. Since a continuous unitary material is typically used, a conceptual boundary shown by dotted line or boundary 22 delineates the first section 20 from the second section 21. The boundary 22 of the optical cap 18 can be imagined as defining a plane positioned distal to the adhesive or protective material 16 that fills the void between the core 14 and the optical cap 18. As shown, in one embodiment a gap is present between the fiber endface 23 (which may be tilted from about 8° to about 15°) and the cavity wall 19. In addition, as shown the adhesive or protective material 16 fills the cavity which includes the coated region 12 and core with cladding 14. The optical element has a curved surface 25 that is distal to the fiber core with cladding 14. The closed distal face/curved endface 25 can include one or more coatings, such as reflecting or partially reflecting coatings. In addition, the optical element and fiber assembly is typically disposed within a sheath 28. In one embodiment, the optical element 18 and the other elements connected or fused thereto rotate together relative to the sheath. In another embodiment, both the sheath 28 and the optical element 18 rotate. In another embodiment, the sheath and optical element 18 are fixed and do not rotate. Also, the region between the sheath and optical element can be filled with fluid.

In one preferred embodiment, the optical element is a monolithic or unitary material. Although combinations of materials can be used to make the optical element, such as mixtures of polymers or glasses, in general the composition of the element is designed to be substantially the same throughout in one embodiment. Coatings or other materials may be applied to, fused with, or otherwise coupled or connected to the unitary optical element.

As shown in the embodiment of FIG. 1, the optical fiber core with cladding 14 and coated region 12 is inserted into a cavity on the proximal side of the optical element 18. Proximal and distal refer to location relative to the end of the fiber that is connected to the instrumentation outside of the body. The cavity (alternatively, fiber receiving chamber of the optical element) defined by wall 19 can be filled with a protective material or adhesive 16 as shown. The adhesive 16 is selected to be substantially optically transparent, and can be cured using ultraviolet light, heat, exposure to air, or any other curing method. To reduce the possibility of bubble formation between the fiber end face 23 and the cavity wall 19, application of the adhesive 16 may be performed under a partial vacuum. The material or adhesive 16 may be chosen to have a refractive index close to that of the fiber 14 and the optical element 18 in order to reduce backreflections. Alternatively, the material or adhesive 16 may be chosen to have a refractive index different than that of the fiber 14 and the optical element 18 in order to produce backreflections with a controlled amplitude. In one embodiment, the adhesive is an acrylic based adhesive. In one embodiment, an ultraviolet light curable adhesive is used.

In one embodiment, the size of the cavity is chosen to be very close to the size of the fiber to prevent tilt issues. The fiber end face is placed in contact with the end of the cavity to prevent longitudinal alignment issues. In one embodiment, this material 16 is an adhesive having a refractive index similar to that of the optical fiber core and the material used to form the element 18, such that back reflections from the fiber tip 23 are further reduced.

When the adhesive is cured (such as by exposure to heat, light, or ultraviolet radiation) the fiber becomes fixed to the cap in the volume or cavity shown. Alternatively, the cap can be formed in place over top of the optical fiber core with cladding 14 and coated portion 12 using a process such as injection molding. Molding the cap directly onto the fiber removes the gluing step and can result in reduced manufacturing costs. Thus, in some embodiments, region 16 comprises the same material filling region 18. That is, when no adhesive 16 is used, the region defined in FIG. 1 is removed and the cap directly contacts the fiber.

The cap is in the general form of a cylindrical tube with a closed distal face. The outer diameter of the optical element 18 is typically on the order of 2× the diameter of the optical fiber, giving an outer diameter range of about 160 µm to about 500 µm. In turn, the inner diameter of the optical element 18 can range from about 80 µm to about 250 µm.

In one embodiment, the cap 18 is made from a single piece of material, chosen to be optically transparent in the spectral band used for the particular imaging or analysis application. In general, the optical elements or caps described herein are suitable for use with imaging applications that use wavelengths of electromagnetic radiation that range from about 350 nm to about 2000 µm. To facilitate low-cost and high-volume manufacturing, the material can be a resin or polymer instead of a glass. If low aberration levels and high transmission are desired for a given application, the cap can also be formed out of glass. Preferred materials include acrylic, polycarbonate, polystyrene, polyetherimide, or polymethylpentene. These materials can be injection molded into parts on the size scale of the optical cap using methods known in the field of micro-molding. Further, these materials are suitable for forming a unitary cap. In general, some embodiments of the elongate unitary cap include an optically transmissive material. As used herein optically transmissive material means a material with low absorption and scattering in the spectral band used for the specific application, such that a substantial fraction of the light radiating from the optical fiber is transmitted.

In one embodiment, a single piece, molded part provides a significant reduction in manufacturing cost and time, and improvement in part-to-part uniformity, compared to miniature optical systems already known in the art as described above. In one embodiment, the length of the optical cap ranges from about 0.25 mm to about 5 mm. The gap between wall 19 and endface 23 ranges from about 0 µm to about 1000 µm.

Light traveling along the optical fiber exits the fiber end face 23 and cavity wall 19 and propagates a length L into the solid material of the second section 21 of the optical element 18. The length L is equal to the distance from the cavity wall 19 to the center of the closed distal surface 25. As the light travels, it will diverge as shown by the first set of dashed lines. Upon reaching the closed distal surface 25, the light interacts with a coating deposited on the outer surface of the distal face.

The coating is designed to be highly reflective in the spectral band used for the particular imaging or analysis application. The coating can be a metal, a single dielectric layer, or a multi-layer dielectric stack. A non-optically-functional layer may be deposited between the distal face and the reflective coating in order to improve adhesion. For example, such a layer can include chrome, titanium, or a dielectric. An additional non-optically-functional layer may be deposited on top of the reflective coating in order to protect the coating from oxidation, peeling, or other damage.

Figure 2A:
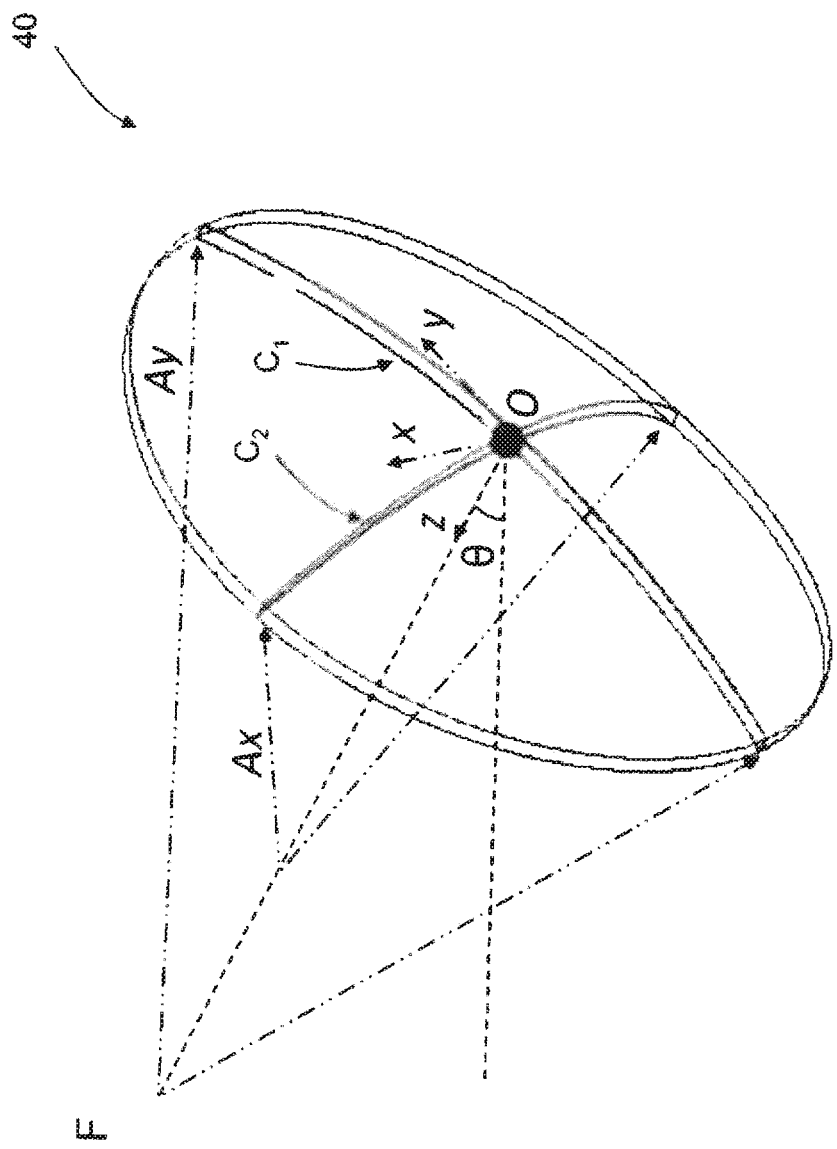
FIGS. 2A-B are three dimensional diagrams that show a reflective lensed end surface and an optical element or cap, respectively, according to illustrative embodiments of the invention.
Figure 3:
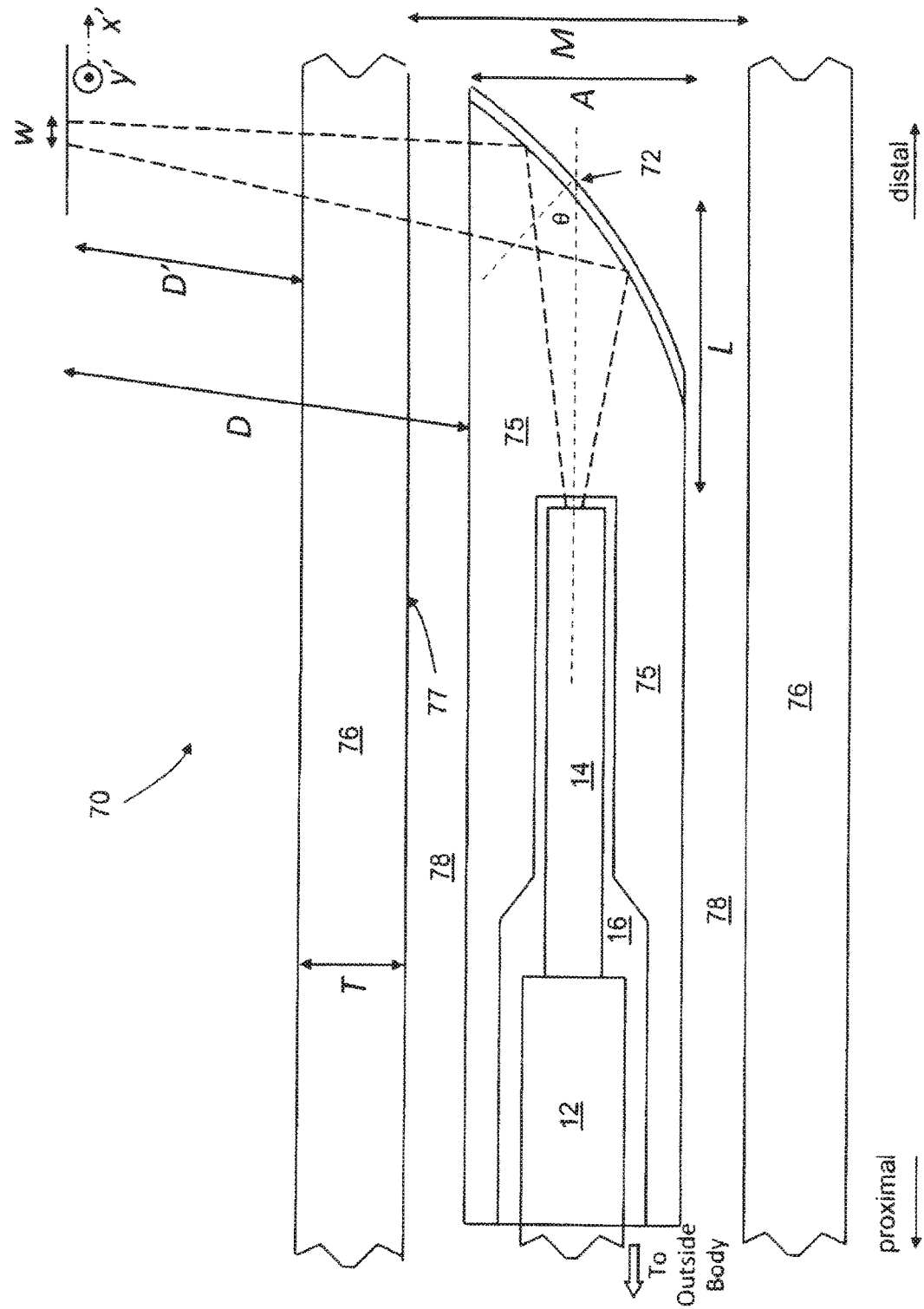
FIG. 3 shows an optical cap surrounding an optical fiber, such that the cap is inside of a transparent sheath according to one embodiment of the invention.

A perpendicular to the center of the distal face 25 is oriented at a tilt angle θ relative to the longitudinal axis of the cap, such that the reflected light is directed at an angle 2θ relative to the incident light (see FIGS. 2A and 3). The distal face 25 is additionally curved to form a focusing surface, the specific details of which are described below.

The light begins to converge or is collimated after interacting with the distal face 25 and reflective coating. As the light passes through the side face of the cap 29 and the sheath 28, it is affected by cylindrical distortion due to the substantiated cylindrical shape of the cap and sheath. This distortion causes the beam to become ovular in cross-section instead of circular, and creates a different focal plane for each of the beam's two major axes. These two focal planes are separated in space along the direction of beam propagation.

Cylindrical distortion is detrimental for many optical analysis applications, since it leads to anisotropic lateral resolution, decreased peak incident power density, and degraded axial resolution. The curvature of the distal face 25, however, can be different in the two orthogonal axes lying in the plane of the distal face, which enables the lens to be optimized to pre-compensate for cylindrical distortion before it occurs. In this way a circularly symmetric beam can be obtained outside of the cap, and the undesirable effects of cylindrical distortion can be avoided. Details of the distal face 25 geometry are described fully below.

Once the light exits the cap, it continues to converge until it reaches a focal plane or focal spot at a working distance D away from the closest edge of the optical element 18. When the fiber is a single-mode fiber, the beam is Gaussian and its size at the focal plane is defined by the focal diameter w which is equal to twice the radius of the Gaussian profile of the beam. In one embodiment, the length L and the geometry of the distal face can be selected to give a wide range of focal spot sizes and working distances. In one embodiment, D is measure as the distance from the side of the cap to the focal plane, along the direction of beam propagation (not necessarily normal to the cap). This approach is consistent with the manner D is illustrated in FIG. 1.

If a long working distance is desired for a particular application, the length L can be increased to allow the beam to expand to a larger diameter prior striking the distal face 25. The beam can expand up to a maximum diameter equal to the outer diameter of the cap, which can range from about 160 µm to about 500 µm. Increased beam expansion on the distal face is equivalent to increasing the aperture of the optical system, which allows the working distance D to be increased for a given focal diameter w. If a small focal diameter w is desired for a particular application, the radius of curvature of the distal face can be decreased. This effectively increases the focal power of the optical system.

End Face Geometry

Figure 2B:
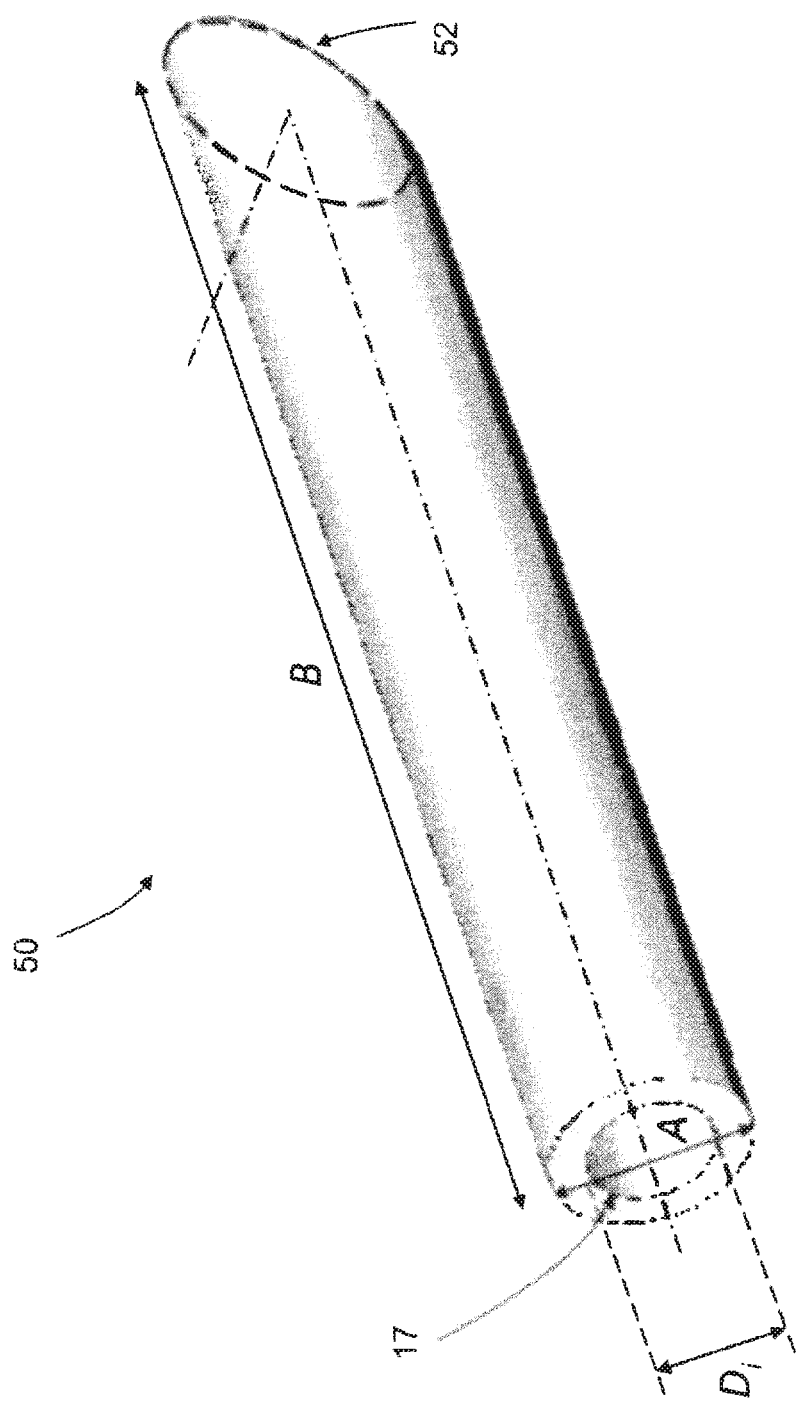

FIG. 2A shows a three-dimensional perspective drawing of the lensed surface 40 (see surface 25 in FIG. 1) with a first focal point $F_1$ and a second focal point $F_2$. FIG. 2B shows a three-dimensional perspective drawing of the entire optical element or miniature optical cap 50, having an outer diameter A, and inner diameter $D_i$, and overall length B. As shown, the cap includes an annular opening 17 sized to receive and fixedly couple to an optical fiber. The focusing or beam forming surface 40 from FIG. 2A is implemented as the surface 52 of FIG. 2B in one embodiment.

In general, in one embodiment, the optical elements are designed to form or direct a substantially circular symmetric beam substantially free of distortions outside of the optical element or cap. To facilitate this design feature, the distal face surface is chosen to have different curvatures along the arcs traced out by rays Ax and Ay that corresponds to the curves $C_1$ and $C_2$, respectively, on the surface 40. Ax and Ay originate from different focal points $F_1$ and $F_2$, respectively. Multiple surface geometries 25, 40 are suitable for the optical elements/caps described herein, including biconic asphere, biconic Zernike, Fresnel, or non-uniform rational B-spline. A biconic asphere surface is generally suitable for applications requiring focal spot sizes of about 3 μm to about 100 μm and working distances of about 0 μm to about 30 mm, and where it is desired to correct for cylindrical distortions caused by the side face of the cap and other materials located between the cap and the focal plane.

Returning to FIG. 2A, the deviation z of the lensed surface away from a flat plane, such as x-y planes, commonly referred to as the surface sag, is defined by the following equation, for a biconic asphere:

$$z = \frac{\frac{x^2}{R_x} + \frac{y^2}{R_y}}{1 + \sqrt{1 - \frac{(1+k_x)x^2}{R_x^2} - \frac{(1+k_y)y^2}{R_y^2}}}$$

When plotted, this equation traces out the shape of the curved surface of the lens and that individual z values correspond to varying surface sag relative to the x-y plane.

In this equation, x, y, and z are local coordinates having an origin O at the center of the surface. $R_x$ and $R_y$ are spherical radii of curvature along the x and y axes, respectively. In the embodiment of FIG. 2A, Ax and Ay are examples of Rx and Ry. Additionally, $k_x$ and $k_y$ are conic constants along the x and y axes, respectively, giving a total of four free parameters for the surface sag z. The surface 40 is also rotated about the x axis to an angle θ, in order to direct the beam of the surface at an angle 2θ. The surface can also be offset in the y direction by an amount $y_{off}$ in order to further reduce aberrations in the optical system.

Optimization of Design Parameters

According to FIG. 3, an optical system 70 including a beam directing surface 72 for directing the beam out a side face of the cap 75 and generating a focal spot at a desired distance from the outer surface of the sheath 76 is shown. Thus, in some embodiments, the beam directing surface both directs and focuses a beam of light or other radiation. Additionally, the curvature of the lensed surface 72 can be adjusted to compensate for distortions caused by transmission through the sheath 76 and the outer cylindrical surface of the cap 75. The following section describes a process for designing a miniature optical cap of the type shown in FIG. 3 in order to achieve a desired focal spot size and working distance that is optimized for a specific optical analysis application. The optical analysis application chosen for this illustrative example is OCT imaging of the coronary blood vessels, which requires the optical fiber and miniature optical cap to rotate and translate longitudinally. This approach offers numerous advantages. These advantages include:

Cost savings from reduced manufacturing time and removing the need for fusion splicing Ability to provide a non-rotationally-symmetric lens shape to compensate for cylindrical distortion Potentially improved repeatability in focal spot size and working distance FIG. 3 shows a miniature optical cap 75 enclosed within a flexible, transparent sheath 76 having an inner diameter M and a wall thickness T. The fiber core with cladding 14, coated region 12, and cap 75 rotate and translate within the sheath by means of an external actuator, while the sheath 76 remains stationary in the blood vessel to prevent damage to the vessel wall.

In this illustrative example, the desired focal spot diameter w is approximately 30 μm. It is desired that the beam reach a focal plane at a distance D' away from the side face of the sheath 76 and a distance D away from the cap, where D' is about 1.6 mm and D is about 1.857 mm. The sheath wall thickness T is about 102 μm and the inner diameter M is about 710 μm. To allow sufficient clearance between the cap and the inner surface 77 of the sheath, the cap outer diameter A is chosen to be about 400 μm. In one embodiment, the cap material is chosen to be acrylic, since this material is optically clear at one wavelength of interest of about 1310 nm.

In this example, to avoid unwanted specular back reflections from the inner surface 77 of the sheath 76, the distal face tilt angle θ is chosen to be about 50° such that the incident light impinging on the distal face is redirected at an angle of about 100° relative to the longitudinal axis of the fiber. The angle θ is shown as being formed between the longitudinal axis of the fiber and a normal vector to the surface 72. Light therefore strikes the inner surface of the sheath 77 at about an angle 10° off normal incidence, and specular backreflections are avoided. In one embodiment, the lumen 78 between the cap and the sheath is filled with radio-opaque contrast fluid having a refractive index of approximately 1.449. Further, in one embodiment the lumen between the sheath 76 and the blood vessel wall is filled with the same contrast material or saline. The contrast material may be provided by a proximal flushing mechanism in order to temporarily displace blood from the vessel and enable a clear OCT image.

The design parameters remaining to be optimized are the distance L from the fiber tip to the lensed surface, the surface sag parameters $R_x$, $R_y$, $k_x$ and $k_y$, and the y offset $y_{off}$ (if any). An optical simulation tool, such as ZEMAX (ZEMAX Development Corporation, Bellevue, Wash.) or an equivalent tool can be used to find the optimal combination of the remaining design parameters to produce the desired focal spot diameter of about 20 μm at a distance of about 1.4 mm from the sheath. This software can also be used to ensure that the resulting beam striking the blood vessel wall is circular and free of aberrations. To accomplish this, an iterative optimization algorithm is employed that searches for the best combination of free parameters to minimize the value of a user-defined error function.

The error function measures several properties of the simulated beam at the focal plane along the local x' and y' axes (See FIG. 3). The measured values are compared to the desired values, and a weighted sum of the difference between the measured and desired values is generated to give the value of the error function. The error function incorporates simulated values of the beam radius at the 13.5% intensity level (corresponding to the characteristic radius, $\omega_0$, of the beam) along the x' and y' axes (Rx and Ry) corresponding to the characteristic beam waist $\omega_0$, Gaussian fit along the x' and y' axes (Gx and Gy), and distance between the desired focal plane and the actual focal plane along the x' and y' axes (Fx and Fy). The error function is constructed to give a zero value when the beam diameters along the x' and y' axes are equal, the Gaussian fit is achieved, and the distance between the desired focal plane and the actual focal plane along the x' and y' axes are equal to zero. When the beam diameters along the x' and y' axes are equal, the beam is circularly symmetric which is desirable for producing an isotropic focal spot. When a Gaussian fit is achieved along the x' and y' axes, the system has minimal distortion which is desirable for maximizing image quality and optimizing the amount of optical power returned to the system for analysis. When these conditions are met, the beam is substantially free of aberration and has the desired focal spot size w at the desired working distance D.

In this illustrative example, the error function E may be chosen to incorporate six parameters, including Rx, Ry, Gx, Gy, Fx, and Fy. Each parameter is additionally assigned a weight W1 through W6, so as to control the relative importance of each parameter in the error function E. Each parameter is also assigned a target value Rxt, Ryt, Gxt, Gyt, Fxt, and Fyt. Rx, Ry, Rxt, Ryt, Fx, Fy, Fxt, and Fyt that can be measured in units of millimeters. Gx, Gy, Gxt, and Gyt are unitless parameters that fall within the range of 0 to 1, with 1 representing a perfect Gaussian fit. The error function E is defined as the weighted sum of each parameter minus its corresponding target value, such that E=W1(Rx−Rxt)+W2(Ry−Ryt)+W3(Gx−Gxt)+W4(Gy−Gyt)+W5(Fx−Fxt)+W6(Fy−Fyt).

In this illustrative example, Rxt and Ryt may be 0.017 mm, corresponding to a full-width-at-half-maximum beam diameter of 0.020 mm. Gxt and Gyt may be 1. Fxt and Fyt may be 0. W1 and W2 may be 50, W3 and W4 may be 0.1, and W5 and W6 may be 1. Each choice of optical design values L, $R_x$, $R_y$, $k_x$, $k_y$, and $y_{off}$ results in a set of beam parameters Rx, Ry, Gx, Gy, Fx, and Fy that in turn results in a particular value for the error function E. With the parameter targets and weights selected, one or more approaches can be used to determine the combination of optical design values L, $R_x$, $R_y$, $k_x$, $k_y$, and $y_{off}$ that results in a minimum error function. This can be achieved by finding either a local minimum in the error function, or a global minimum in the error function. Many optical design packages, such as ZEMAX, contain built-in optimization algorithms that are adequate for performing this step.

In this illustrative example, the results of the optimization process give a value for L of about 721 μm, $R_x$ of about −772 μm, $R_y$ of about −1675 μm, $k_x$ of about −3797 μm, $k_y$ of −about 15,970 μm, and $y_{off}$ of about −23 μm. With these values implemented in an optical fiber cap embodiment, a focal spot size can be formed of about 29.6 μm in diameter at a distance D' of about 1600 μm. Such a focal spot size is suitable to perform OCT imaging and data collection in the coronary blood vessels.

Exemplary Focal Spot Sizes and Working Distances

Figure 4:
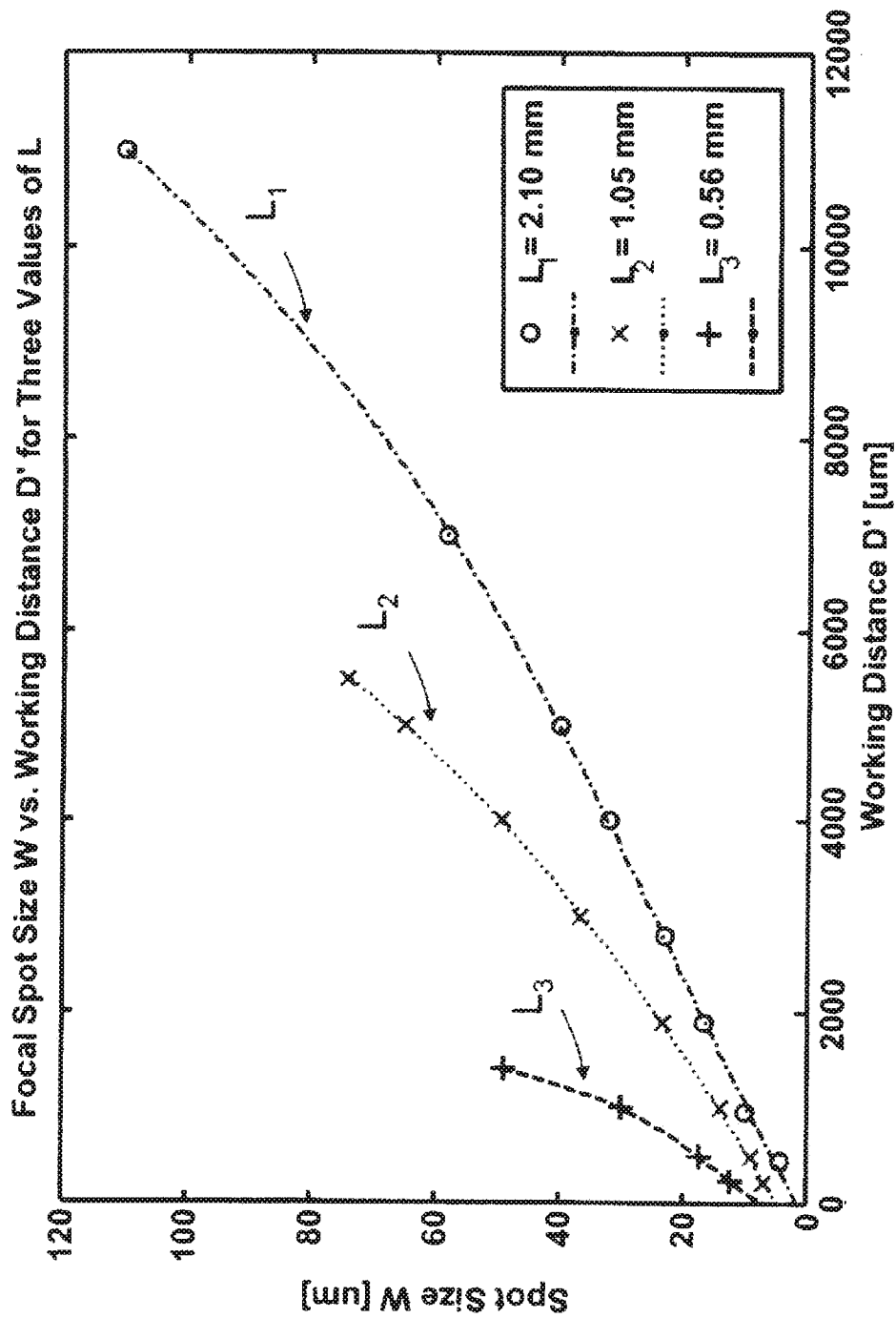
FIG. 4 shows an exemplary range of focal spot sizes and working distances for three different lengths of solid material between an optical fiber tip and lensed reflective surface of an optical cap according to an illustrative embodiment of the invention.

Embodiments of the optical components such as the caps or beam forming elements described herein enable a wide range of focal spot sizes and working distances by building miniature optical caps with different distal face surface geometries and different distances L ($L_1$, $L_2$, and $L_3$) between the fiber tip and distal face. $L_1$, $L_2$, and $L_3$ are chosen for illustrative purposes and do not limit the scope of the invention. In one embodiment, $L_2$ was chosen to be half of $L_1$, and $L_3$ is half of $L_2$. As an illustrative example, an acrylic cap with an outer diameter of about 400 μm is used to depict various data points as shown in FIG. 4. Specifically, FIG. 4 illustrates a subset of the design parameters available for an acrylic cap as discussed above, where the distance L from the fiber tip to the distal end face is chosen to be one of about 2.10 mm, about 1.05 mm, or about 0.56 mm, respectively. These particular values of L are chosen for illustrative purposes only and do not limit the scope of the invention. At each point on each curve, the end face geometry was optimized according to the method described above, using an error function as described above, in order to obtain a focal spot at a given working distance.

FIG. 4 shows that for this particular type of end cap, focal spot sizes of about 4.3 μm to about 110 μm can be achieved at working distances of about 0 mm to about 11 mm. For any given length L, the maximum working distance D' occurs when the focal spot size approaches the size of the beam incident on the distal end face. Under this condition, the focusing power of the optical system is weak and the working distance cannot be further extended.

Internal Lensed Surface

Figure 5:
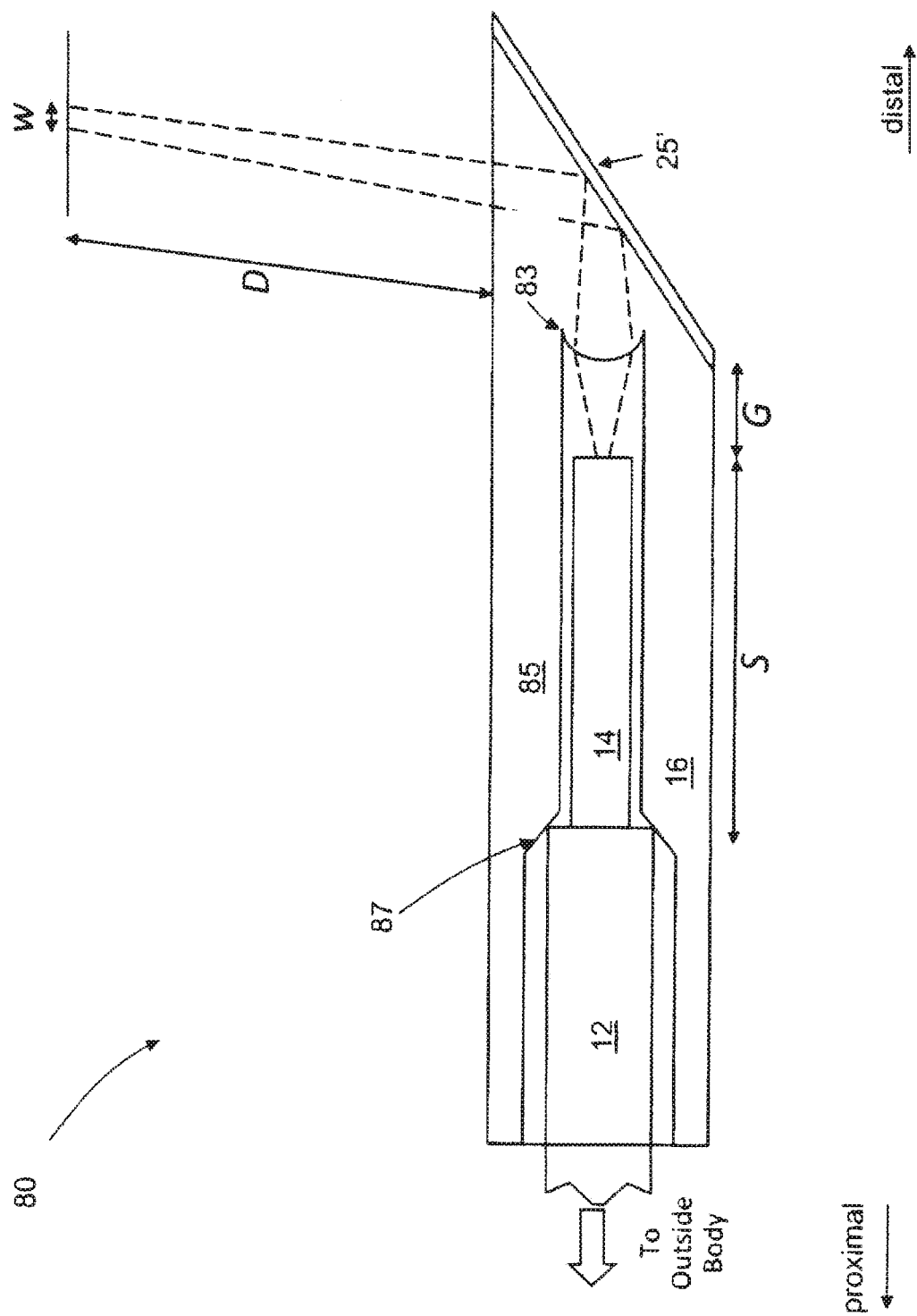
FIGS. 5 and 6 show an optical cap that includes a transmissive lensed internal surface and an angled reflective end surface for directing a beam through a side face of a cap and generating a focal spot at a desired distance from the cap, according to an illustrative embodiment of the invention.

FIG. 5 shows another optical subsystem 80 of the present invention, where beam focusing is provided by an internal lensed surface 83 at the end of the cavity instead of by the distal end face. The cap 85 has a different cavity shape because of the additional lensed surface 83. The surface 83 can be concave or convex, can have different radii of curvature in the x and y axes, can be spherical or aspheric or any other type of surface generally known in the art of lens design. The surface 83 allows for beam collimation or beam focusing and other features. In general the shape of surface 83 may be of the same form as the shape shown in FIG. 2A. Surface 83 can be any type of lens surface. The surface 83 can be of the same form as the shape shown in FIG. 2A, where the tilt angle theta can be as low as zero degrees. This surface 83 serves as a boundary between the cavity and beam forming sections of the cap 85 akin to boundary 19 in FIG. 1. Beam direction is still provided by the distal end face 25', although in this embodiment the end face is angled and flat.

In one embodiment, the end face 25' is made reflective by coating it with a reflective material such as metal or a dielectric coating. In this embodiment, light radiating from the fiber tip expands into a gap G. The gap may be filled with an optical adhesive, so as to join the fiber 14 to the cap 85, or it may alternatively be filled with air to allow more rapid beam expansion. The length of the gap G is set by the length S of the fiber where the protective coating has been removed, and by the length of the cavity S+G.

In one embodiment, a taper 87 on the proximal side of the cavity acts as a stop against the coated portion of the fiber, such that the insertion length of the fiber can be precisely controlled. Alternatively, a cylindrical stop may be used in place of a taper, although tapered features are generally preferred for micro-molding fabrication processes. In micro-molding processes, sharp edges are difficult to fabricate. The gap length G and the surface sag of the internal surface can be optimized in a manner analogous to the one described above using an error function. If the cap 85 is to be placed inside of a sheath (not shown), it is understood that the gap length G and the surface sag for surface 83 can be further optimized to correct for distortions caused by transmission through the sheath.

This cap embodiment 85 provides several benefits in addition to those described above for the cap design shown in FIG. 3. First, the lensed surface 83 is located within a cavity, protecting it from accidental damage during handling or operation. Second, the area of the internal lensed surface 83 is smaller than that of the distal end face 25', which simplifies the tool design used to fabricate the cap. Third, because the distal end face 25' is flat instead of curved, achieving a uniform coating layer thickness is simplified. Coating adhesion may also be improved because of the flatness of the end face.

Dual Lensed Surfaces

Figure 6:
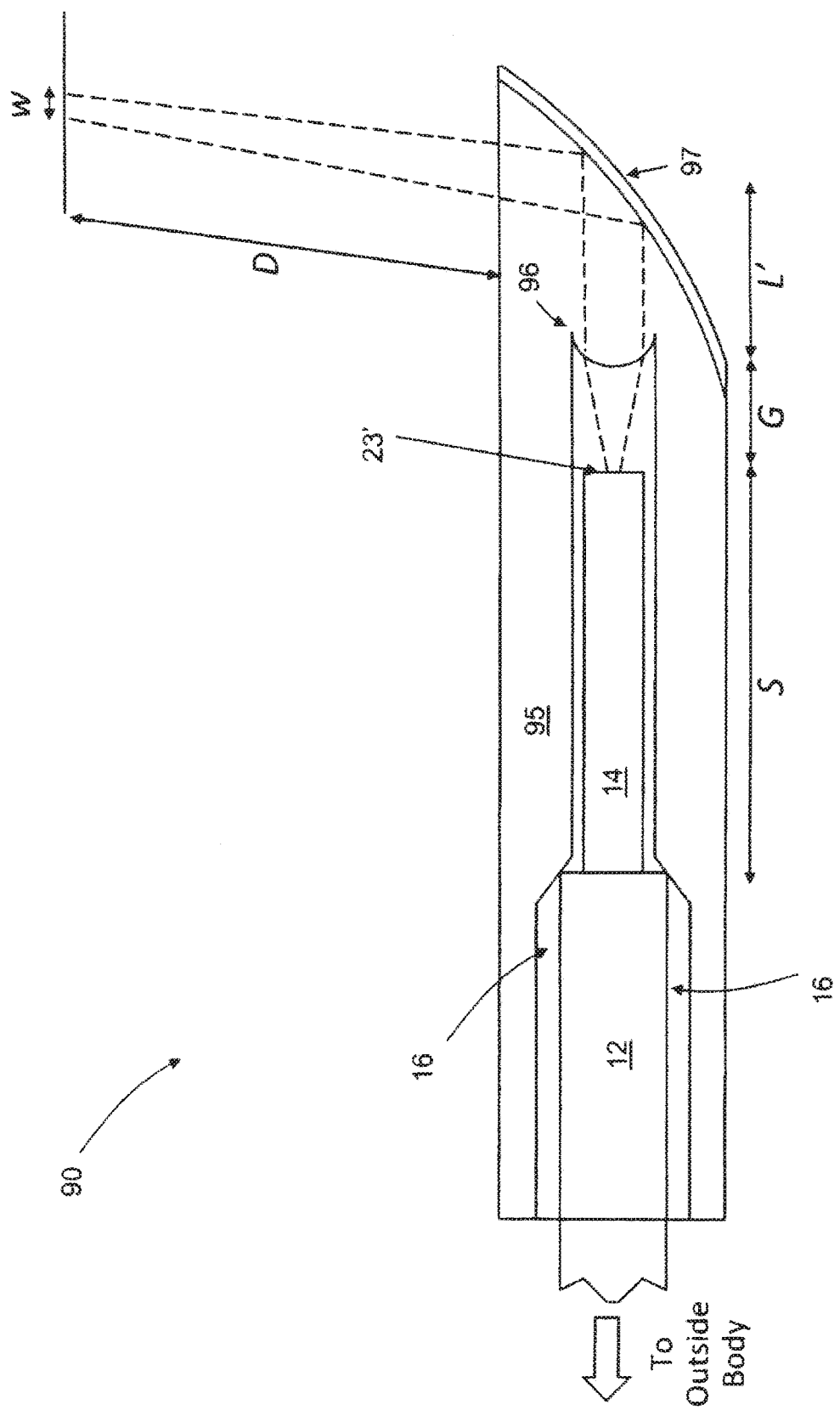

FIG. 6 shows another optical subsystem 90 with a cap embodiment 95, where beam focusing is provided by a combination of one internal lensed surface 96 at the end of the cavity and a reflective lensed surface 97 formed on the distal end face. Beam direction is still provided by making the end face 97 reflective by coating with a reflective material such as metal or a dielectric coating. In this embodiment, light radiating from the fiber tip 23' expands into a gap G. The light refracts upon interaction with the internal lensed surface 96 and propagates through a length L' of solid material. The light then impinges on the distal end face 97, where it is further focused and redirected out a side face of the cap. The gap length G, the solid material length L', and the surface sags of the internal surface 96 and distal end face 97 can be optimized in a manner analogous to the one described above using an error function. If the cap 95 is to be placed inside of a sheath, it is understood that the gap length G and the surface sag of both surface 96 and surface 97 can be further optimized to correct for distortions caused by transmission through the sheath.

Figure 8:
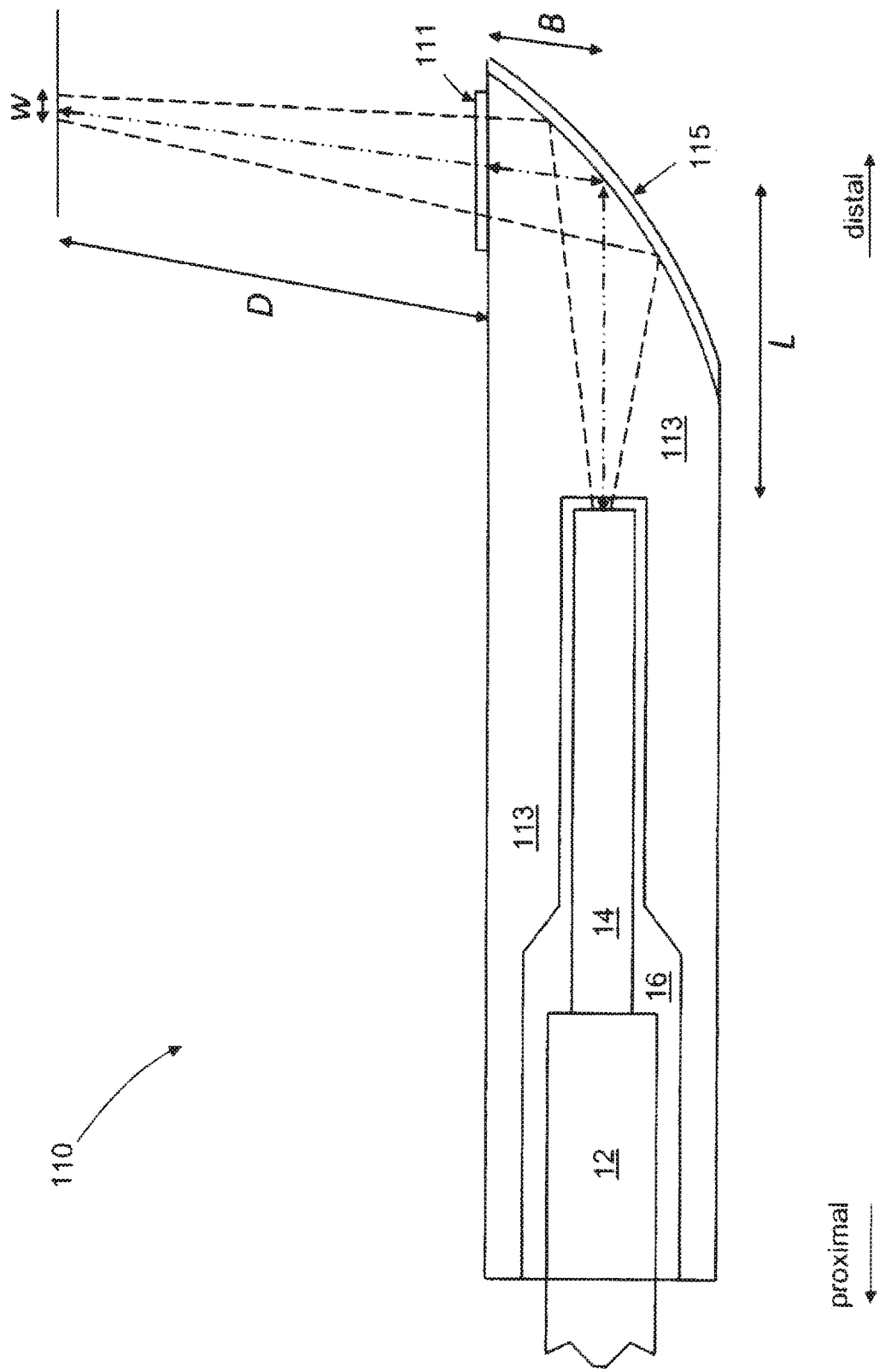
FIG. 8 shows an optical cap that includes a curved, reflectively lensed end surface for directing the beam out a side face of the cap through a coating disposed on the outer cylindrical surface of the cap according to an illustrative embodiment of the invention.
Figure 11:
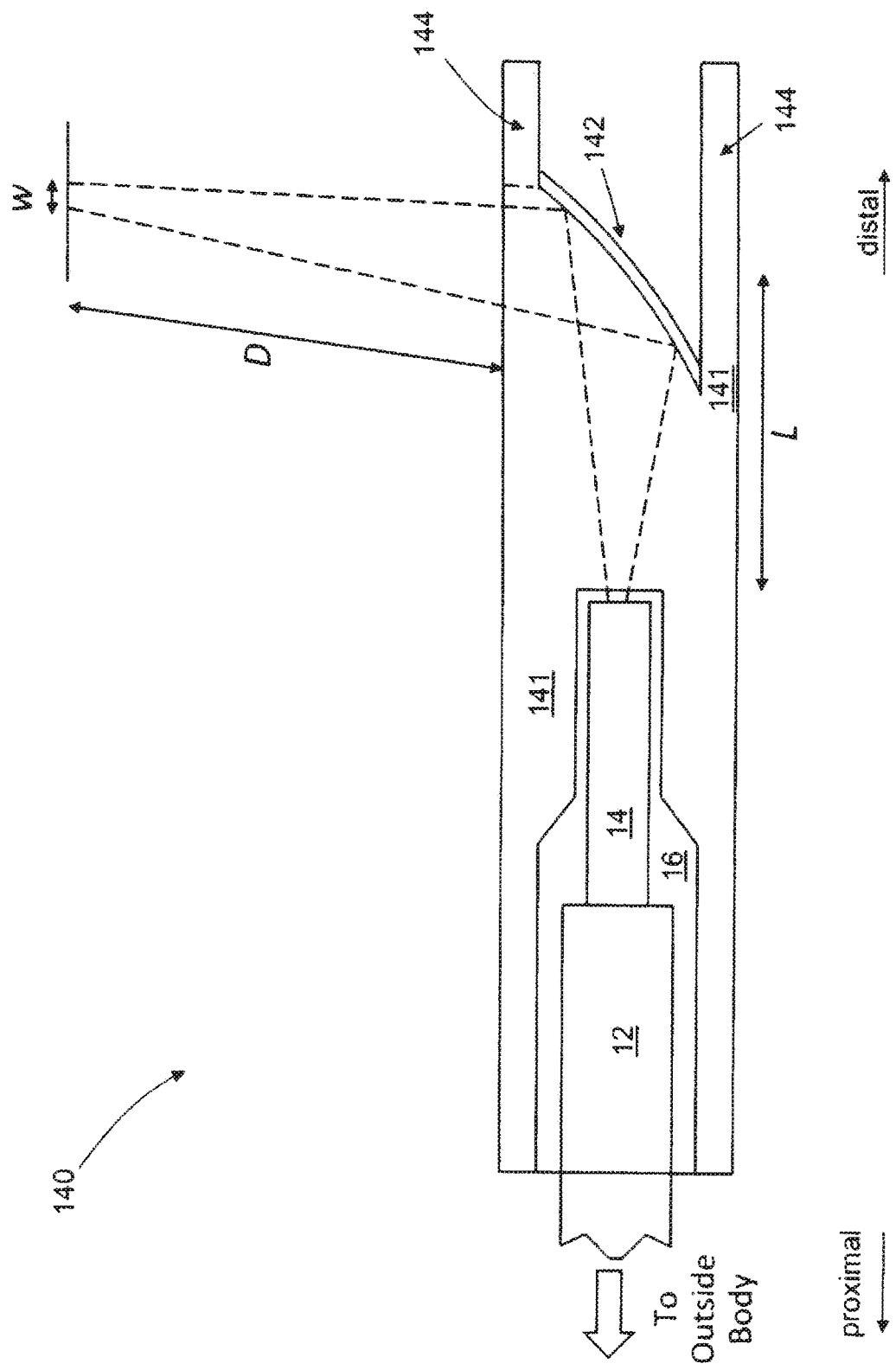
FIG. 11 shows an optical cap in which the reflective lensed surface is partially shielded from damage by locating it partially within a body of the cap, according to an illustrative embodiment of the invention.

This cap embodiment 95 provides several benefits in addition to those described above for the cap designs shown in FIG. 3 and FIG. 5. First, the use of two lensed surfaces 96, 97 provides more free design parameters and allows a wider range of focal spot sizes w and working distances D to be obtained. Second, the use of two lensed surfaces results in fewer geometric aberrations than a comparable design using a single lensed surface, improving the optical quality of the resulting beam. Third, the internal lensed surface 96 and gap G can be configured such that the light transmitted into the length L' of solid material is substantially collimated. In this way, the exact value of L' becomes less critical to the overall optical performance of the system, thereby improving the design's tolerance to fabrication errors. Under certain manufacturing conditions, the embodiments show in FIG. 3, 8 or 11 are preferred embodiments.

Partially Reflecting End Face for Dual Beam Scanning

Figure 7:
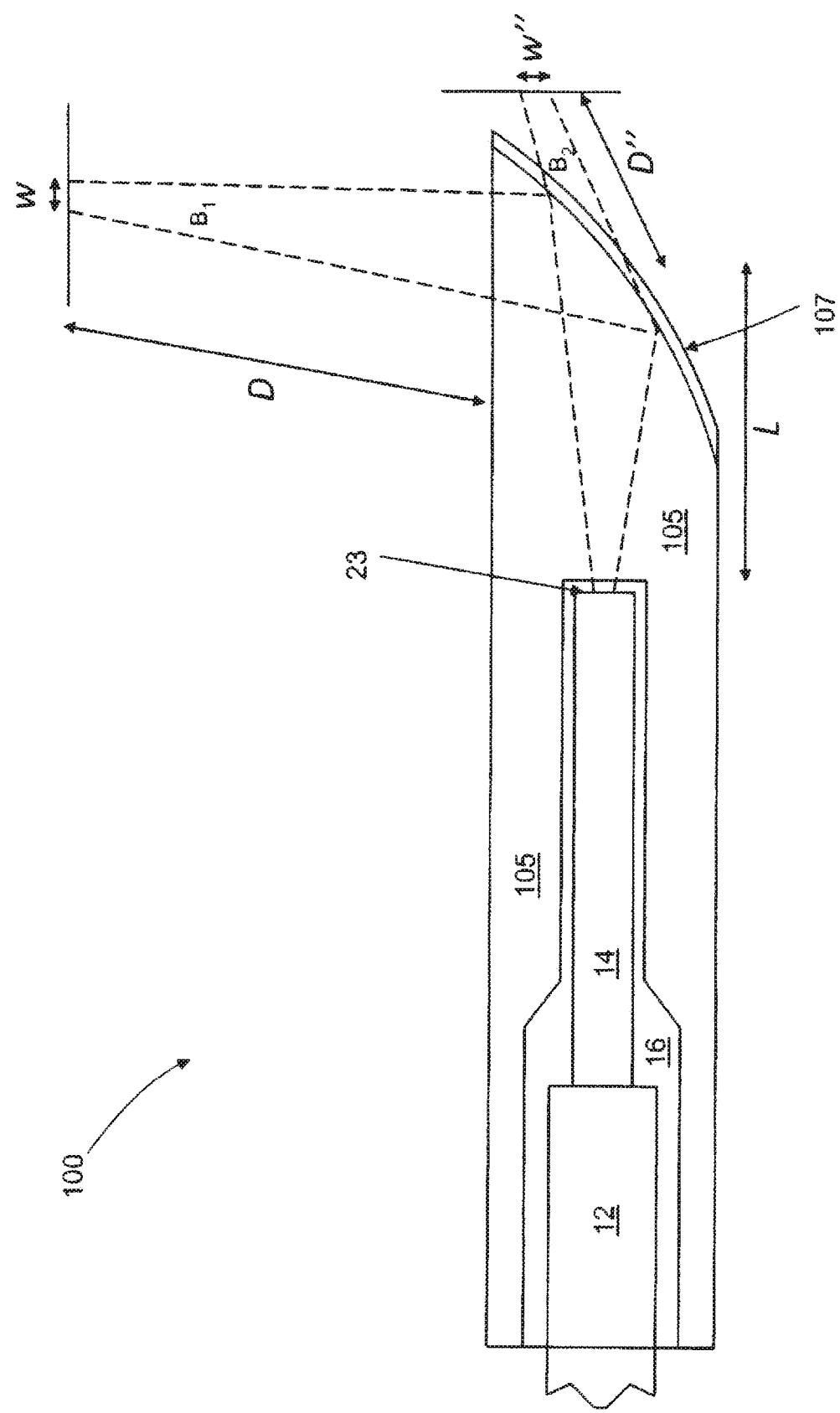
FIG. 7 shows an optical cap that includes a curved, partially-reflective lensed end surface for generating two focused beams directed through a side face and end face of the cap, according to an illustrative embodiment of the invention.

FIG. 7 shows another system embodiment 100 of the present invention that uses a cap 105, where light radiating from the tip 23 of the fiber is split into two focused beams $B_1$, $B_2$ by a partially-reflecting coating on the distal end face 107 of the miniature optical cap 105. In this embodiment, light radiating from the fiber tip 23 expands into a length L of solid material. The light impinges on the distal end face 107, where it interacts with a partially reflecting coating that transmits a portion of the light through the end face and reflects another portion of the light through the side face of the cap. The reflected portion of the light $B_1$ reaches a focal plane at a first working distance D with a focal spot size w. The transmitted portion of the light $B_2$ reaches a second focal plane at a second working distance D" with a second focal spot size w". If the cap is to be placed inside of a sheath, it is understood that the solid length L and the distal end face surface sag can be further optimized to correct for distortions caused by transmission through the sheath.

The partially-reflecting coating referenced above can be formed in several ways. First, a highly reflective material such as metal can be applied in a pattern on the distal end face such that the metal covers less than 100% of the end face area exposed by the beam. The pattern can include a checkerboard, annulus, concentric rings, or any other pattern. Second, a dielectric coating can be applied over a continuous portion of the end face area. The properties of the dielectric material can be selected to partially reflect a fixed fraction of the incident optical power. Alternatively, the dielectric coating can be selected to substantially reflect one wavelength band and to substantially transmit a second wavelength band. This type of coating is commonly referred to as a "dichroic" or "dichroic mirror" coating.

The embodiment of FIG. 7 provides several benefits in addition to those described above for the cap designs shown in FIG. 3, FIG. 5, and FIG. 6. First, generation of two beams $B_1$, $B_2$ along different axes allows simultaneous analysis of two different sample locations. This facilitates examining luminal structures inside the body. One illustrative example is OCT imaging of a blood vessel containing an occlusive lesion. Using this embodiment, forward-looking annular images can be obtained at the same time as side-looking radial images by rotating the catheter about the axis of the fiber. In this way, OCT images can be obtained from in front of the catheter as it is advanced into the lesion in order to analyze the lesion makeup.

More generally, forward imaging is useful for guiding the placement of an imaging catheter to avoid perforating a luminal wall. If a dichroic coating is employed, an additional benefit is the ability to conduct optical analysis of a sample in front of the cap using one group of wavelengths, and optical analysis of a sample beside the cap using a second group of wavelengths. Thus, using such an approach it is possible to conduct multimodal imaging of a luminal structure. OCT imaging can be conducted using about 1310 nm light directed through the side of the cap, while confocal fluorescence imaging can be conducted using about 800 nm light directed through the front of the cap.

Fixed Reflection Surfaces

In several optical analysis and data collection applications, including OCT imaging, it is desirable to include one or more surfaces that generate reflections of known intensity at known positions relative to the focal plane. This facilitates calibration and interferometer calculation in some embodiments. A fixed reflection can be used in OCT applications to generate a calibration signal for adjusting the reference arm length to match the sample arm length (See U.S. Pat. App. Pub. No. 2009/0122320, Petersen et al.) The disclosures of which are incorporated by reference in their entirety.). A fixed reflection can also be used to generate a reference field that interferes with the light returned from the sample in OCT applications. As a result, this forms a common-path interferometer within the imaging catheter and avoids the need for a separate reference arm.

In part, the present invention enables the generation of fixed reflections including a calibration signal only, a reference field only, or both a calibration signal and a reference field. FIG. 8 shows a system 110 embodiment of the invention where a coating 111 is applied to a region of the side face of the miniature optical cap 113. Typically, a partially-reflective or backscattering coating 111 is applied to a portion of the side face of the optical cap to generate a controlled reflection at a known distance from the focal spot. As shown, the coating 111 overlaps the region of the side face where the beam exits the cap 113. The coating 111 is chosen to be partially transmissive, which can be achieved by using a patterned metal coating, a thin-film dielectric stack, or small backscattering particles. By using the coating 111, a fixed portion of light will be reflected by the coated portion of the side face. This reflected light impinges again on the curved distal face 115 and is coupled back into the optical fiber 14.

The amount of reflected light that is desired to be coupled back into the fiber 14 depends on whether the fixed reflection will be used to generate a calibration signal or a reference field. If an OCT calibration signal is desired, the intensity of the light coupled back into the fiber 14 from the fixed reflector 115 should be similar to the intensity of light returned from the sample in order to prevent saturation of the detection system.

If an OCT reference field is desired, the intensity of the light coupled back into the fiber 14 from the fixed reflector 115 should be several orders of magnitude higher than the intensity of light returned from the sample. This provides sufficient heterodyne gain to the sample light and thereby obtains sufficient detection sensitivities for imaging in scattering tissue. However, since the coating 111 is not located at the focal plane of the optical system, and since it is placed on the cylindrically curved side face of the cap, the back reflected light will not be perfectly coupled into the fiber. Therefore the reflectivity or backscattering fraction of the coating is typically selected such that it is sufficiently high to compensate for these fiber coupling losses, which can be calculated with optical design tools commonly used in the field.

Figure 9:
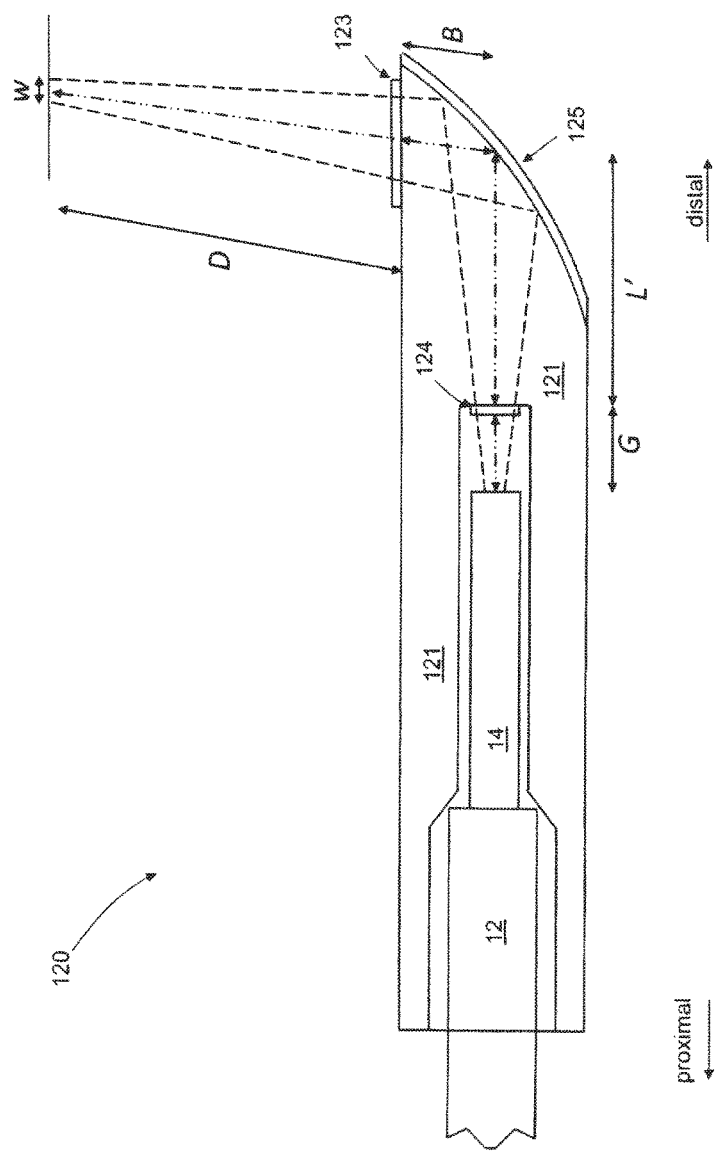
FIG. 9 shows an optical cap that includes reflective or partially reflective surfaces in addition to a curved and reflective lensed surface according to an illustrative embodiment of the invention.

FIG. 9 shows another system embodiment 120 where two fixed reflections are provided by two coatings. Specifically, in one embodiment, partially-reflective or backscattering coatings are applied to a portion of the side face and an internal face of the optical cap 121 for generating two controlled reflections at known distances from the focal spot. One coating 123 is located on a portion of the side face of the cap, and the other coating 124 is located on a portion of the internal surface of the cavity that receives the optical fiber 14. By generating two fixed reflections, the miniature optical cap 14 can provide one calibration signal and one reference field. Alternatively, two calibration signals can be provided or two reference signals can be provided.

Distal Tip Designs for Optical Surface Protection

Figure 10:
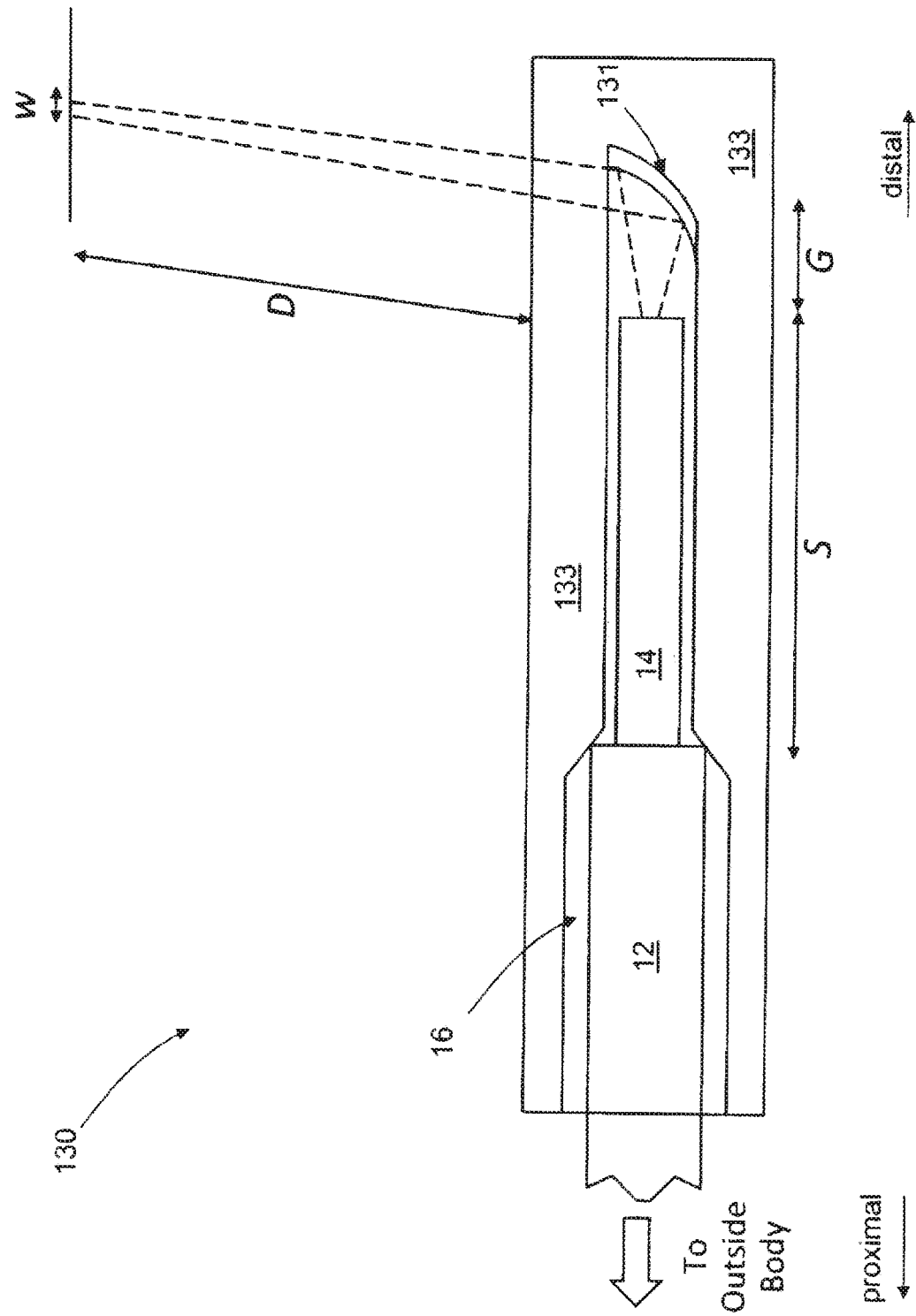
FIG. 10 shows an optical cap in which the reflective lensed surface is protected from damage by locating it inside a volume defined within the cap, according to an illustrative embodiment of the invention.

For some analysis applications, it is desirable to protect the optical surfaces of the miniature end cap from damage that may occur during catheter assembly or during operational use of the device. FIG. 10 illustrates a system 130 that protects the optical surface 131 by disposing it within the optical element or cap 133. Beam focusing is provided by an internal lensed surface at the end of the cavity that receives the fiber. Beam direction is provided by the same internal surface by tilting the surface relative to the longitudinal axis of the fiber. The internal surface is made reflective by coating with a reflective material such as metal or a dielectric coating.

FIG. 11 shows a system 140 with an optical element 141 that provides partial protection of the optical surface 142, which may be sufficient to prevent damage in many applications. In this embodiment, the optical surface 142 is located within a recess formed by extending the cylindrical wall 144 of the cap distally beyond the end face. In this embodiment, the fiber 14 resides in a first cavity formed in the optical element or cap 141 and the light directing surface 142 is formed in a second cavity formed at the distal end of the cap 141.

Optical Coherence Tomography Imaging

The various embodiments of miniature optical caps described here are well-suited for conducting OCT imaging of internal luminal structures. A flexible OCT imaging catheter can be constructed by enclosing the optical cap and fiber within a transparent sheath that covers the length of the catheter. The fiber and cap can then be rotated about the longitudinal axis of the fiber to conduct side-directed spiral imaging. Rotational motion can be coupled from a motor outside of the body by use of a torque cable. These various combinations of elements can operate as a data collection probe as shown in the system embodiments of the applicable figures. Forward-directed annular images may also be obtained if the cap is configured to generate a forward-looking beam in addition to the side-looking beam, as shown in FIG. 11.

Figure 12:
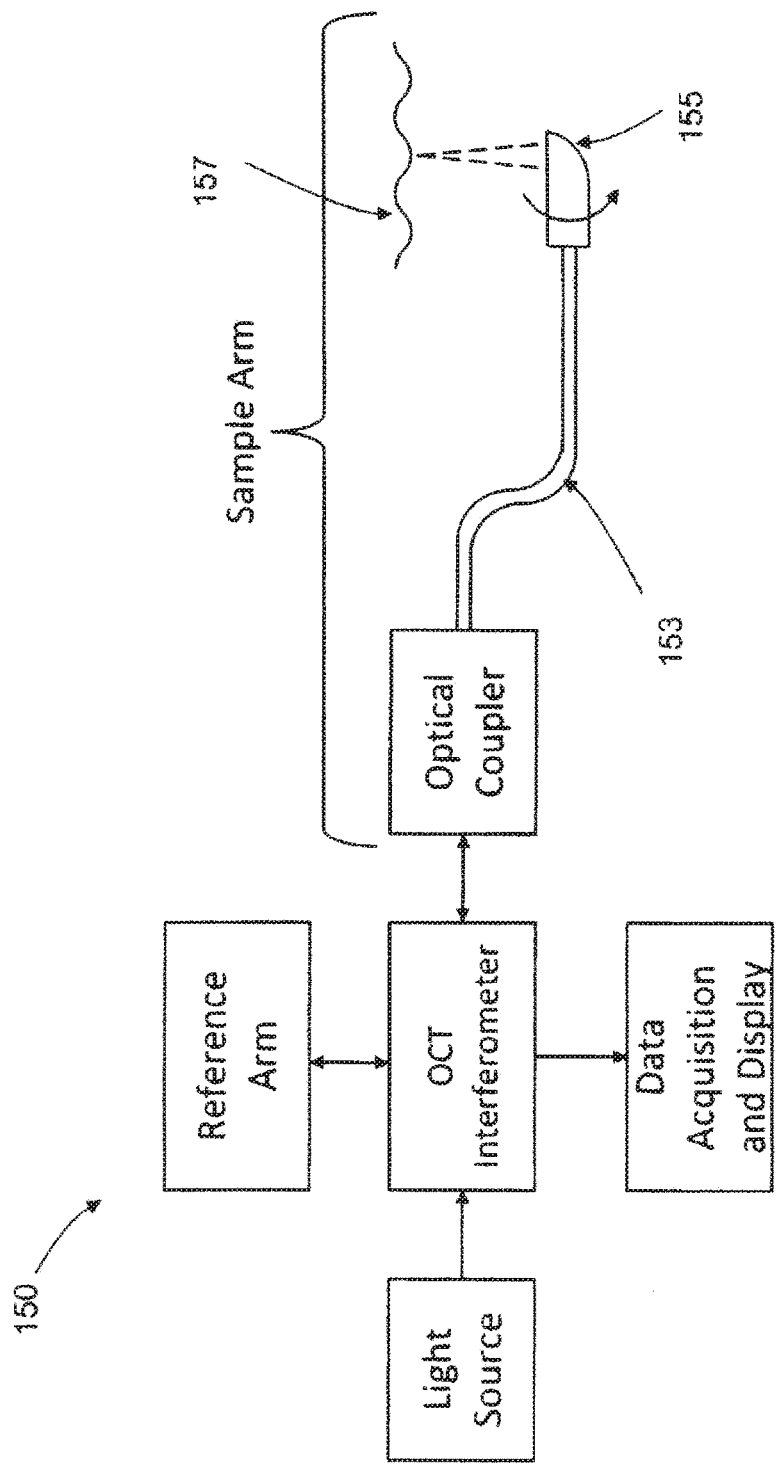
FIG. 12 shows an apparatus for conducting optical coherence tomography data collection according to an illustrative embodiment of the invention.

FIG. 12 shows a data collection system 150 for conducting OCT imaging with a flexible catheter that includes a miniature optical cap 155 at its distal tip. The optical cap 155 is fixed to a flexible optical fiber 153 to form an insertable imaging catheter, which directs light onto a sample 157 and returns sample arm light to the OCT interferometer. A light source is in optical communication with an OCT interferometer, which can be a Michelson interferometer or any variant thereof that is known in the field. The light source can be a broadband superluminescent diode, a tunable laser with a narrow instantaneous linewidth and broad tuning range, a supercontinuum source, or any source of low-coherence optical radiation. The OCT interferometer is in optical communication with a reference arm, which generates a reference field that interferes with sample light returned from the sample arm.

The sample arm comprises an optical coupler and a flexible imaging catheter. The optical coupler connects to the proximal end of the catheter, directing a portion of the radiation from the light source into the catheter. The optical coupler also provides rotational and translational motion, which is translated to the distal tip of the catheter and the miniature optical cap. Light is guided down the fiber, focused and redirected by the miniature optical cap 155, and impinges on the sample. As shown, the fiber and cap combination can rotate. Backscattered and back reflected light from the sample is collected by the miniature optical cap and transmitted back down the fiber, through the optical coupler, and into the OCT interferometer. The sample and reference arm light interferes, and is then detected, processed, and displayed by a data acquisition and display system.

Figure 13:
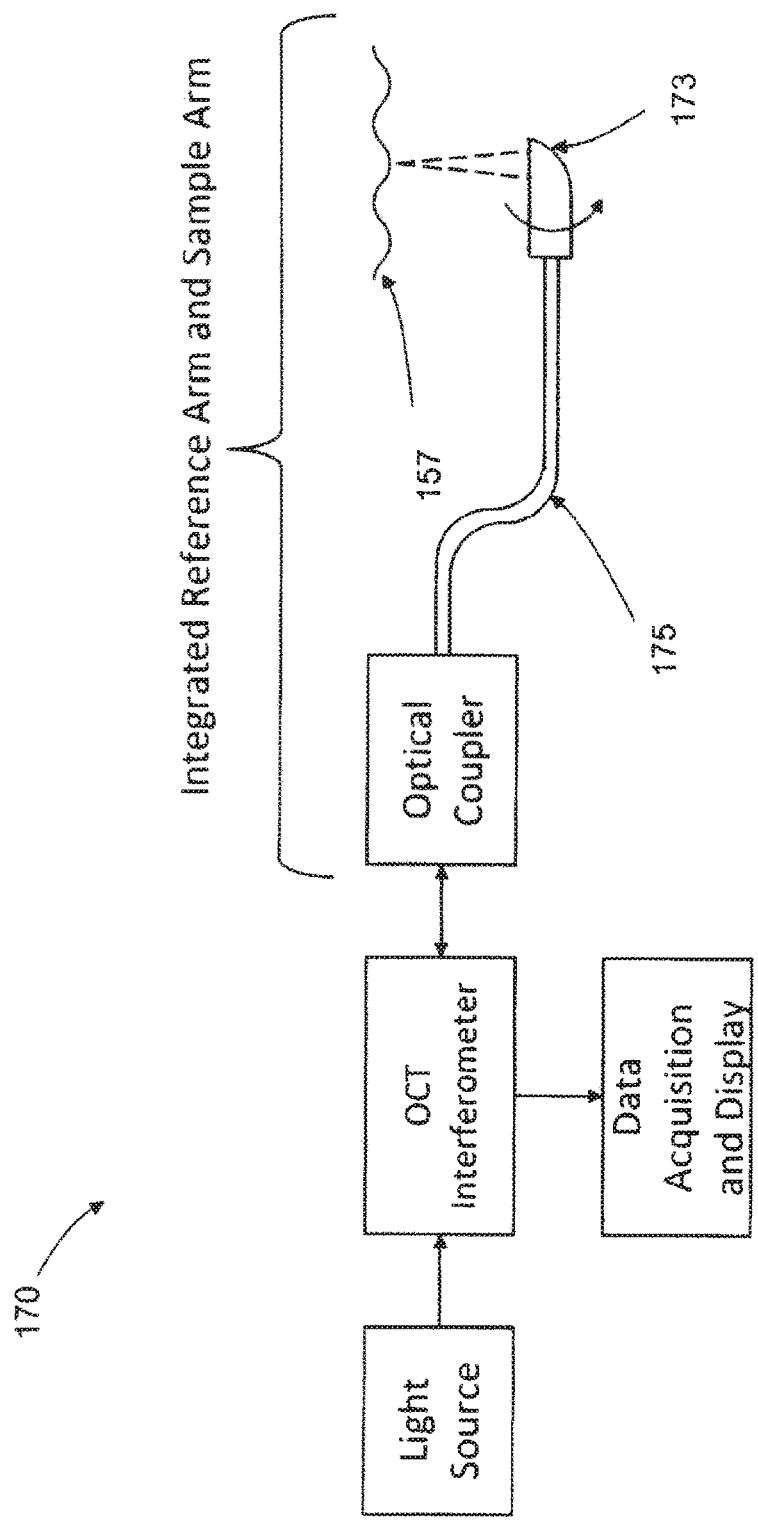
FIG. 13 shows a second apparatus for conducting optical coherence tomography data collection according to an illustrative embodiment of the invention.

FIG. 13 shows another system 170 for conducting OCT imaging with a flexible catheter that includes a miniature optical cap 173 at its distal tip, the optical cap having at least one fixed reflecting surface as shown in FIG. 8 or FIG. 9. The optical cap is fixed to a flexible optical fiber 175 to form an insertable imaging catheter, which directs light onto a sample and returns sample arm light to the OCT interferometer. Additionally, the optical cap 173 generates a fixed reference reflection at a known position relative to the focal plane. The reference reflection acts as an interferometric reference field and interferes with the sample light to form optical coherence tomography image lines. This configuration is known as a "common path" interferometer in the field of OCT imaging. Common path interferometers embodiments offer the advantage of matching optical aberrations such as chromatic and polarization-induced dispersions in the sample and reference arms as they are common mode (the sample and reference fields are generated after traveling through a substantially the same physical path). In turn, matching these types of aberrations improves image resolution and contrast. However, certain types of common-mode noise can no longer be cancelled. Overall, the benefits of a common-path interferometer often outweigh the disadvantages, once a practical method for building the common-path design has been established.

In this case, the fixed reflecting surface is configured to produce a reference field that interferes with the sample light returned from the sample. The optical coupler and flexible catheter therefore comprise an integrated reference arm and sample arm. This arrangement has many benefits compared to the apparatus shown in FIG. 12. First, since there is no separate reference arm, the system cost and complexity are reduced. In a traditional OCT interferometer, a reference arm having the same length as the sample arm is required. In this embodiment, the reference field is generated very close to the sample and therefore the reference arm path length is inherently matched to the sample arm path length.

Manufacturing Process and Mold Embodiments

Figure 14A:
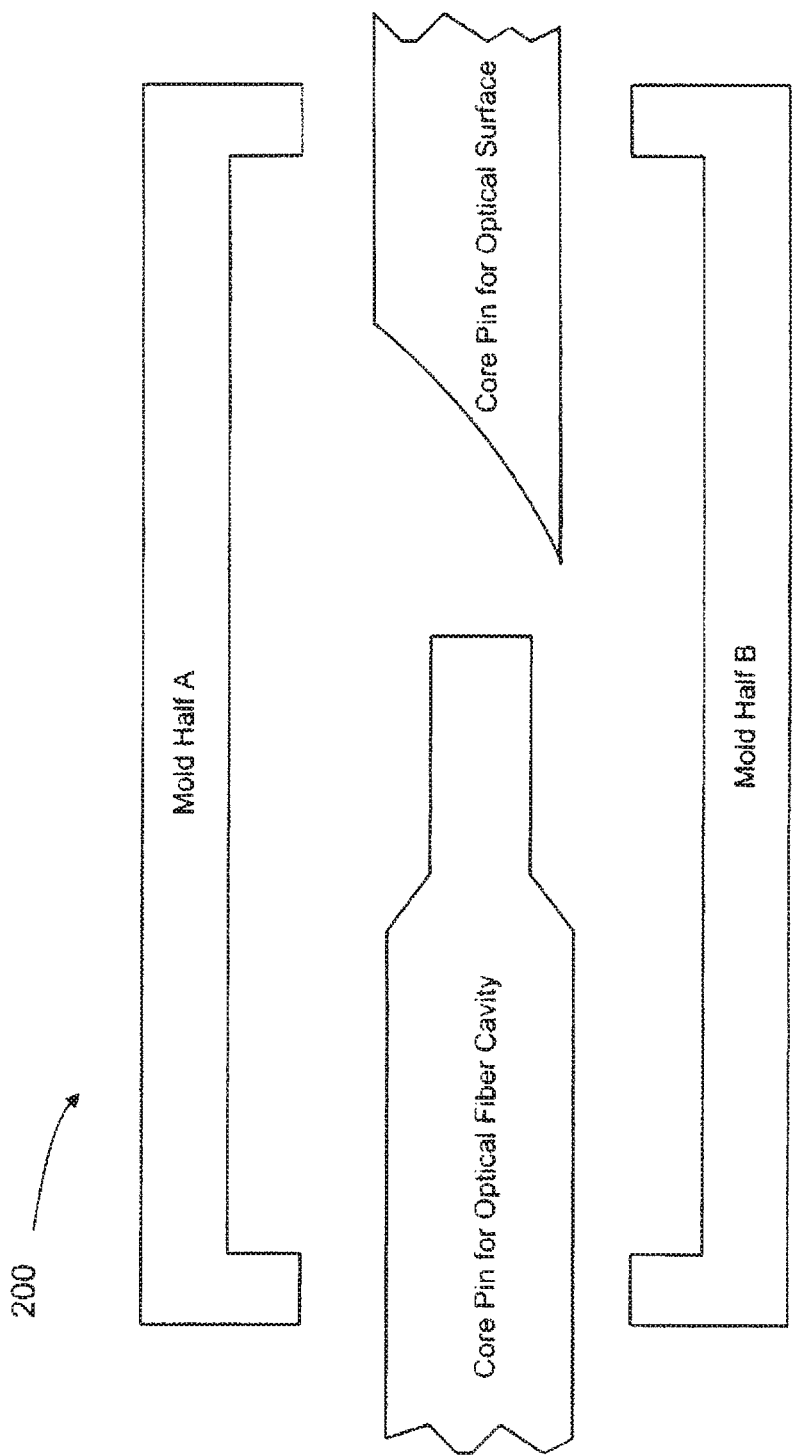
FIG. 14A shows a mold for fabricating an embodiment of the invention.
Figure 14B:
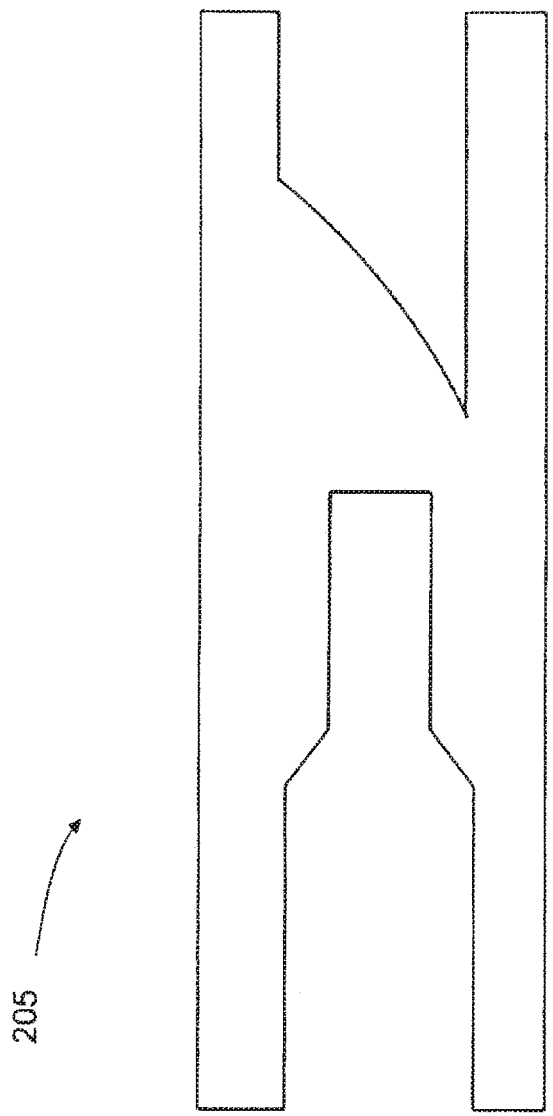
FIG. 14B shows an embodiment of the invention fabricated using the mold depicted in FIG. 14A.

Any of the embodiments of the present invention can be manufactured from a single piece of material in one step or multiple steps, followed by application of coatings in subsequent steps. Alternatively, multiple pieces of material can be joined together in single or multiple steps. To achieve a small manufacturing cost and rapid manufacturing time, the manufacturing process can be of any type of molding, including injection molding, compression molding, or a specialized type of injection molding known as micro-molding. FIG. 14A shows a mold 200 containing four components used to produce an embodiment of the present invention with a molding process. A large two-part clamshell can be used to form the elongate cylindrical shape of the cap. A first core pin, with a with a gradual change in diameter from approximately the outer diameter of the coated fiber region to the outer diameter of the core and cladding region, can be used to form the cavity that receives the optical fiber. A second core pin, with a diameter approximately equal to the diameter of the closed end face of the cap, can be used to form the optical surface at the end of the cap. Essentially, the core pins are disposed in the mold and the material which will form the final molded part flows and solidifies around the pins and the FIG. 14B shows a molded part 205 that can be obtained using the mold tool 200 shown in FIG. 14A.

Optical-quality surface finishes can be attained by diamond-turning the ends of the core pins. This process reduces aberrations from surface roughness and thereby improves image quality. Furthermore, the use of core pins allows the optical surfaces to be formed from a single molded piece, rather than machining half of the optical surface on each of the two clamshell mold pieces that form the cylindrical body of the cap. Alternatively, the first core pin may be replaced in the micro-molding process by the optical fiber itself. This arrangement, known in the field as "molding in place" or "over-molding", positions the optical fiber in half-cavities formed in the two clamshell components of the mold.

Figure 15A:
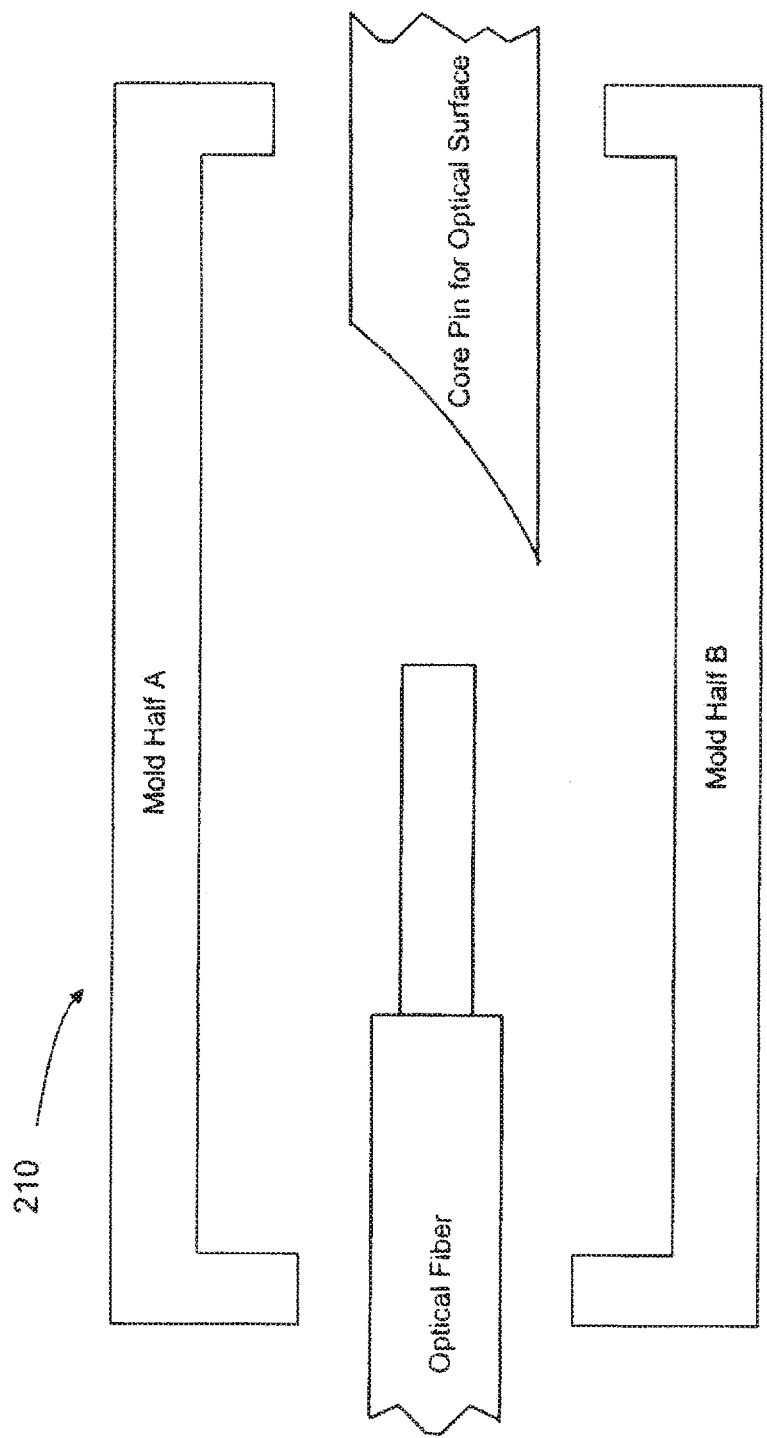
FIG. 15A shows a mold for fabricating an embodiment of the invention.
Figure 15B:
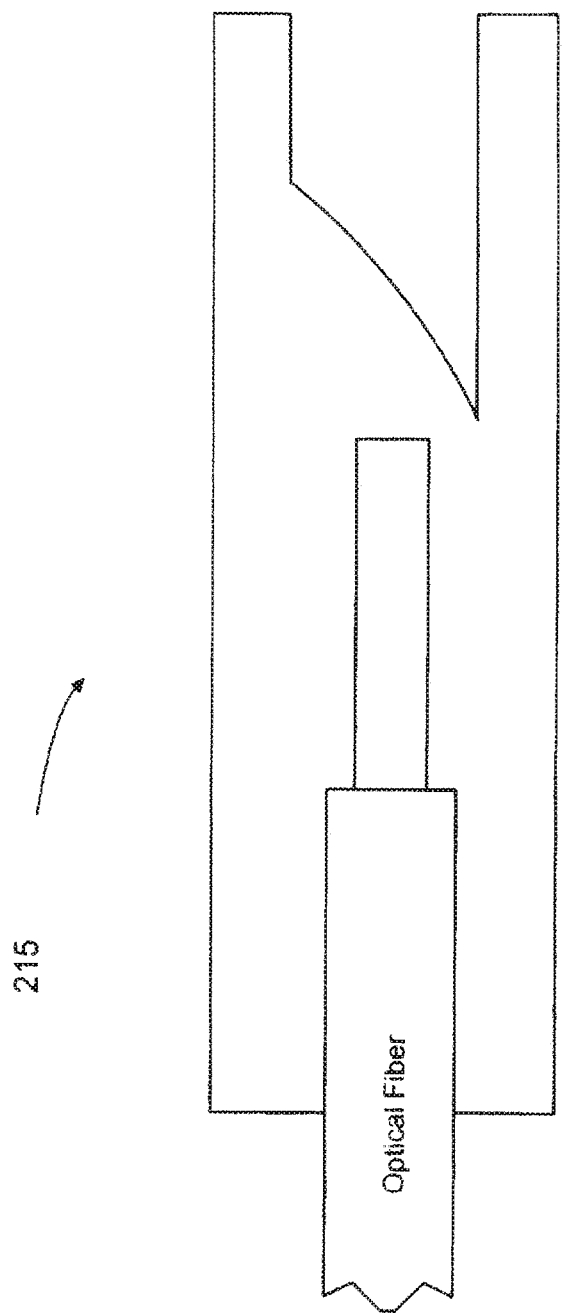
FIG. 15B shows an embodiment of the invention fabricated using the mold depicted in FIG. 15A.

FIG. 15A shows a mold 210 containing three components used to produce an embodiment of the present invention with an over-molding process. In an over-molding process, the optical fiber takes the place of the core pin that would have formed the cavity that receives the optical fiber. During the molding process, the melted polymer flows directly over the fiber and hardens in place, forming the molded part directly on the fiber. Since this process incorporates the fiber into the molded part, it precludes the need for gluing or separately joining the fiber into the cavity of the molded part during subsequent assembly steps. FIG. 15B shows a molded part 215 that can be obtained using the mold tool shown in FIG. 15A, where the optical fiber is joined to the elongate cap directly during the over-molding process.

Integrated Reference Reflector and Scattering Particle Embodiments

Figure 16:
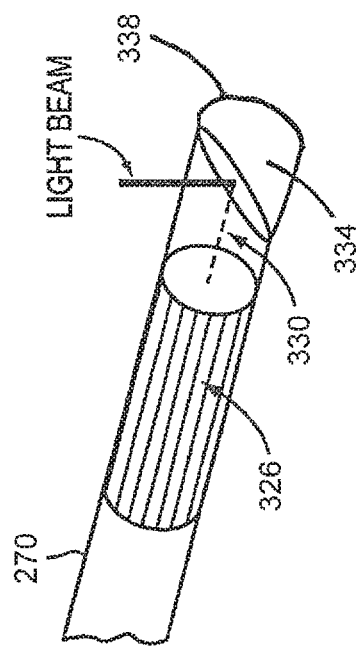
FIG. 16 is a schematic diagram of the optical fiber tip, with micro lens and protective cover.

FIG. 16 depicts an embodiment of the image wire tip of the probe. The optical fiber 270 terminates in a micro-lens assembly 326 which focuses the light at a distance from the micro-lens assembly 326. Light emitted from the micro-lens assembly 326 is reflected by a beam deflector 330 so to as to pass at substantially right angles to the optical axis of the fiber 270. The entire fiber assembly is covered by a protective transparent sheath 334 which has been doped with a small amount of scattering material to provide a reference reflection corresponding to the sample arm path length. This reflection is most useful in a non-common-path interferometers (the more typical type), as the sample and reference optical paths are physically distinct, yet must be path-length matched to create the required interference signal.

Several materials exist as a suitable dopant. In particular titanium dioxide ($TiO_2$) is advantageous. $TiO_2$ is used in many paint formulations due to its excellent light scattering properties. Further it is inert and can be made in bulk. The particle size can be made much smaller than the optical wavelengths of interest (nominally 1.3 µm), making the scattering 'Rayleigh' in nature. Thus the outgoing and returning light wavefronts are not appreciably disturbed, thereby minimizing any potential image degradation at sufficiently low concentrations of dopant.

In addition, because OCT imaging has tremendous sensitivity and large dynamic range (typically 100 dB of sensitivity and >60 dB of dynamic range can be achieved in practical instruments) care must be used to calculate then achieve the optimal doping level of $TiO_2$ in the material.

Basic scattering theory can be used to arrive at a doping concentration in the material. In a typical OCT image in the coronary arteries, the minimum noise in the instrument is about −100 dB. That is, about 1 ten-billionth of the optical output power applied to the object of interest and a typical image has approximately 40 dB of useful dynamic range. The image processing electronics and software are optimized for this range, so the probe reflector element should be optimized to be near the maximum detectable peak of the image intensity, which is about −60 dB (−100+40). This means that the probe reflector should be the brightest object in the image.

As described herein the probe reflector element can include, but is not limited to, a membrane, a film, a cap, a cover, or other material. In some embodiments, the reflector element is flexible or inflexible. The reflector element can be shaped in various geometries, such that portions of the reflector are curved, planar, or substantially planar.

Basic scattering theory for particles and classic radar cross-section theory estimates that the fraction of light reflected from a single $TiO_2$ particle is given by the expression:

$$L_R = \frac{\sigma_b}{V_i} l_c \Delta\Omega$$

where $L_R$ is the return light fraction, $\sigma_b$ is the scattering cross-section (calculated from standard MIE theory), $V_i$ is the volume of the particle, $l_c$ is the interaction length (from Radar theory), in this case the coherence length of the OCT light, and $\Delta\Omega$ is acceptance angle (solid angle) of the micro-lens. Thus, for a particle size of roughly 45 nm with a scattering cross section of approximately $4.26 \times 10^{-7}$ µm², and light having a coherence length of about 15 µm irradiating the particle through a micro-lens having a solid angle of ~0.004, the reflected light fraction, $L_R$, is about 0.006, or −32 dB.

Figure 17:
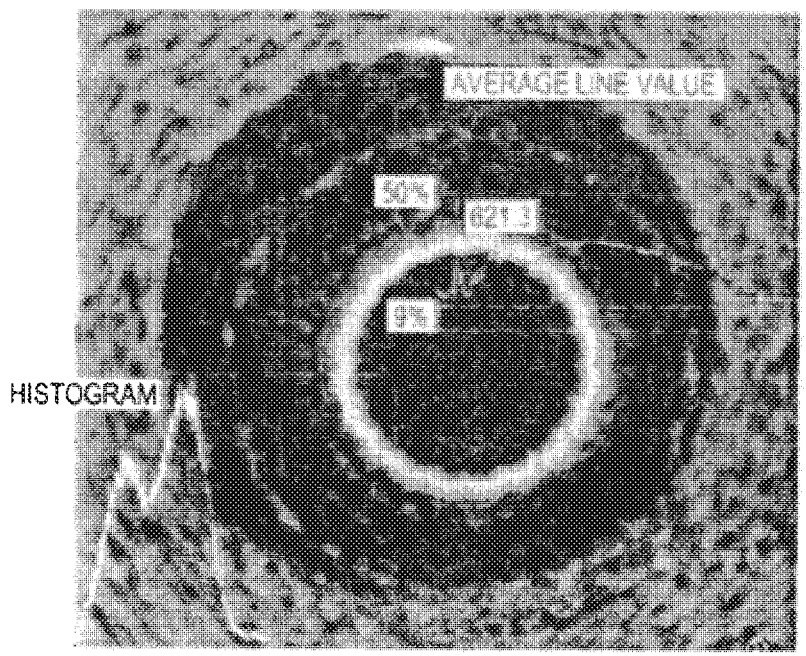
FIG. 17 depicts an image taken with a doped plastic lens cover.

Therefore the total light returned from the probe reference reflector element material should be equal to the single particle light fraction times the volume fraction (doping concentration). Because this should be equal to about −60 dB (from above), a reduction of −30 dB (or 0.001) is required. Therefore, the volume fraction should be about 0.001, or about 0.1% doping concentration by volume. This should result in a strong, but not overpowering reference reflection by the $TiO_2$ particles, as shown in FIG. 17.

Having thus described certain embodiments of the present invention, various alterations, modifications, and improvements will be apparent to those skilled in the art. Such variations, modifications and improvements are intended to be within the spirit and scope of the invention. Accordingly, the foregoing description is by way of example only and is not intended to be limiting.

What is claimed is:

1. An optical beam directing element comprising:
a unitary optical element having a longitudinal axis,
the unitary optical element defining a channel sized to receive an optical fiber,
the unitary optical element comprising a beam directing surface angled and positioned relative to the longitudinal axis such that divergent light received from the optical fiber positioned in the channel is directed a working distance D from outer surface of the a unitary optical element to form a focal spot having diameter w.

2. The optical beam directing element of claim 1 further comprising an adhesive, the adhesive secures the optical fiber in the channel.

3. The optical beam directing element of claim 2 wherein the adhesive is optically transmissive.

4. The optical beam directing element of claim 1 wherein the channel terminates at a boundary defined by a surface of the unitary optical element.

5. The optical beam directing element of claim 2 further comprising a stationary sheath and the optical fiber, wherein the optical fiber is disposed within the sheath, the optical fiber and the unitary optical element arranged to rotate within the stationary sheath.

6. The optical beam directing element of claim 1 further comprising an intravascular imaging probe comprising a sheath and the optical fiber wherein the unitary optical element and the optical fiber are disposed within the sheath.

7. The optical beam directing element of claim 1 wherein the beam directing surface is a biconic asphere.

8. A method of imaging a blood vessel using an optical coherence tomography probe comprising an optical fiber and a unitary optical element in optical communication therewith, the method comprising:
transmitting light from a light source along the optical fiber, wherein the optical fiber has an endface such that divergent light propagates from the endface;
transmitting the divergent light through a beam directing surface of the unitary optical element such that distortion compensated light propagates from the beam directing surface;
transmitting the distortion compensated light through an outer surface of the unitary optical element and a flexible sheath surrounding the unitary optical element; and
imaging a blood vessel, using light scattered from the blood vessel, in response to light received from the flexible sheath.

9. The method of claim 8 further wherein the step of imaging the blood vessel includes generating an image of the blood vessel using optical coherence tomography.

10. The method of claim 8 further comprising reflecting light from the beam directing surface in response to a coating disposed thereon.

11. The method of claim 8 further comprising transmitting the divergent light from the endface of the optical fiber.

12. The method of claim 8 wherein the beam directing surface is a biconic asphere.

13. The optical beam directing element of claim 1 wherein D ranges from about 0 μm to about 30 mm.

14. The optical beam directing element of claim 1 wherein w ranges from about 3 μm to about 100 μm.

15. The optical beam directing element of claim 1 wherein at least a portion of the beam directing surface is coated with a reflecting coating.

16. The optical beam directing element of claim 1 wherein a partially reflective coating is disposed within the channel.

17. The optical beam directing element of claim 1 wherein the beam directing surface is selected from the group consisting of asphere, biconic Zernike, Fresnel, and non-uniform rational B-spline.

18. The method of claim 8 further comprising generating a reference signal in response to a reflecting element disposed within the unitary optical element.

19. The method of claim 8 further comprising directing the distortion compensated light is a working distance D from the outer surface to form a focal spot having diameter w.

20. The method of claim 19 further comprising splitting the distortion compensated light such that a second optical beam is directed a working distance D' from the outer surface to form a focal spot having diameter w'.

* * * * *